(12) United States Patent
Delfyett et al.

(10) Patent No.: US 9,022,037 B2
(45) Date of Patent: May 5, 2015

(54) LASER ABLATION METHOD AND APPARATUS HAVING A FEEDBACK LOOP AND CONTROL UNIT

(75) Inventors: Peter Delfyett, Geneva, FL (US); Richard Stoltz, Plano, TX (US)

(73) Assignee: Raydiance, Inc., Petaluma, CA (US)

( * ) Notice: Subject to any disclaimer, the term of this patent is extended or adjusted under 35 U.S.C. 154(b) by 1681 days.

(21) Appl. No.: 11/224,867

(22) Filed: Sep. 12, 2005

(65) Prior Publication Data

US 2006/0084957 A1 Apr. 20, 2006

Related U.S. Application Data

(63) Continuation-in-part of application No. 10/849,585, filed on May 19, 2004, now abandoned, and a continuation-in-part of application No. 10/916,367, filed on Aug. 11, 2004, now Pat. No. 7,143,769, and a (Continued)

(51) Int. Cl.
*A61B 19/00* (2006.01)
*A61B 18/20* (2006.01)
*A61B 17/00* (2006.01)
*A61B 18/00* (2006.01)

(52) U.S. Cl.
CPC ........ *A61B 18/20* (2013.01); *A61B 2017/00057* (2013.01); *A61B 2018/00636* (2013.01)

(58) Field of Classification Search
USPC ...................... 606/3–12; 607/88–94; 128/898
See application file for complete search history.

(56) References Cited

U.S. PATENT DOCUMENTS

| 2,436,662 | A | 2/1948 | Norgaard |
| 3,459,960 | A | 8/1969 | Aaland et al. |
| 3,549,256 | A | 12/1970 | Brienza et al. |
| 3,599,019 | A | 8/1971 | Nannichi et al. |
| 3,602,836 | A | 8/1971 | Young |
| 3,622,907 | A | 11/1971 | Tomlinson et al. |
| 3,626,318 | A | 12/1971 | Young |
| 3,628,179 | A | 12/1971 | Cuff |

(Continued)

FOREIGN PATENT DOCUMENTS

| EP | 214100 A | 3/1987 |
| EP | 691563 A2 | 1/1996 |

(Continued)

OTHER PUBLICATIONS

Yeh et al., "Theory of Bragg Fiber", Journal of the Optical Society America, Sep. 1978, pp. 1196, vol. 68, No. 9.

(Continued)

*Primary Examiner* — Ahmed Farah
(74) *Attorney, Agent, or Firm* — Haverstock & Owens LLC

(57) ABSTRACT

A laser ablation method and apparatus uses a laser device to generate a pulsed laser using a laser device and to project the pulsed laser onto an ablation target to be ablated. A probe is then used to measure an indicative property of the ablation target or of the pulsed laser projected on the ablation target. A control loop is used to optimize ablation effect by generating a feedback signal according to the measured indicative property, sending the feedback signal to a control unit, and adjusting an output parameter of the pulsed laser according to the feedback signal. The measured indicative property may be a size of the laser beam spot or a material composition. The ablation, the feedback and the adjustment may be performed dynamically.

21 Claims, 4 Drawing Sheets

Related U.S. Application Data continuation-in-part of application No. 10/916,368, filed on Aug. 11, 2004, now abandoned, and a continuation-in-part of application No. 10/916,365, filed on Aug. 11, 2004, now Pat. No. 7,367,969, and a continuation-in-part of application No. 10/850,325, filed on May 19, 2004, now abandoned, and a continuation-in-part of application No. 10/849,586, filed on May 19, 2004, now abandoned, and a continuation-in-part of application No. 10/849,587, filed on May 19, 2004, now abandoned.

(60) Provisional application No. 60/494,275, filed on Aug. 11, 2003, provisional application No. 60/494,274, filed on Aug. 11, 2003, provisional application No. 60/494,273, filed on Aug. 11, 2003, provisional application No. 60/494,322, filed on Aug. 11, 2003, provisional application No. 60/494,267, filed on Aug. 11, 2003, provisional application No. 60/494,172, filed on Aug. 11, 2003, provisional application No. 60/503,578, filed on Sep. 17, 2003.

(56) References Cited

U.S. PATENT DOCUMENTS

| | | | |
|---|---|---|---|
| 3,631,362 | A | 12/1971 | Almasi et al. |
| 3,646,469 | A | 2/1972 | Buczek et al. |
| 3,654,624 | A | 4/1972 | Becker et al. |
| 3,696,308 | A | 10/1972 | Duffy et al. |
| 3,735,282 | A | 5/1973 | Gans |
| 3,764,641 | A | 10/1973 | Ash |
| 3,806,829 | A | 4/1974 | Duston et al. |
| 3,808,549 | A | 4/1974 | Maurer |
| 3,851,267 | A | 11/1974 | Tanner |
| 3,942,127 | A | 3/1976 | Fluhr et al. |
| 3,963,953 | A | 6/1976 | Thornton, Jr. |
| 4,061,427 | A | 12/1977 | Fletcher et al. |
| 4,194,813 | A | 3/1980 | Benjamin et al. |
| 4,289,378 | A | 9/1981 | Remy et al. |
| 4,389,617 | A | 6/1983 | Kurnit |
| 4,394,623 | A | 7/1983 | Kurnit |
| 4,449,215 | A | 5/1984 | Reno |
| 4,590,598 | A | 5/1986 | O'Harra, II |
| 4,622,095 | A | 11/1986 | Grobman et al. |
| 4,655,547 | A | 4/1987 | Heritage et al. |
| 4,673,795 | A | 6/1987 | Ortiz, Jr. |
| 4,718,418 | A | 1/1988 | L'Esperance, Jr. |
| 4,722,591 | A | 2/1988 | Haffner |
| 4,730,113 | A | 3/1988 | Edwards et al. |
| 4,750,809 | A | 6/1988 | Kafka et al. |
| 4,808,000 | A | 2/1989 | Pasciak |
| 4,815,079 | A | 3/1989 | Snitzer et al. |
| 4,824,598 | A | 4/1989 | Stokowski |
| 4,827,125 | A | 5/1989 | Goldstein |
| 4,829,529 | A | 5/1989 | Kafka |
| 4,835,670 | A | 5/1989 | Adams et al. |
| 4,847,846 | A | 7/1989 | Sone et al. |
| 4,848,340 | A | 7/1989 | Bille et al. |
| 4,849,036 | A | 7/1989 | Powell et al. |
| 4,856,011 | A | 8/1989 | Shimada et al. |
| 4,878,127 | A | 10/1989 | Zollman et al. |
| 4,902,127 | A | 2/1990 | Byer et al. |
| 4,907,586 | A | 3/1990 | Bille et al. |
| 4,913,520 | A | 4/1990 | Kafka |
| 4,915,757 | A | 4/1990 | Rando |
| 4,928,316 | A | 5/1990 | Heritage et al. |
| 4,947,398 | A | 8/1990 | Yasuda et al. |
| 4,950,268 | A | 8/1990 | Rink |
| 4,972,423 | A | 11/1990 | Alfano et al. |
| 4,983,034 | A | 1/1991 | Spillman, Jr. |
| 4,988,348 | A | 1/1991 | Bille |
| 4,994,059 | A | 2/1991 | Kosa et al. |
| 5,010,555 | A | 4/1991 | Madey et al. |
| 5,014,290 | A | 5/1991 | Moore et al. |
| 5,022,042 | A | 6/1991 | Bradley |
| 5,031,236 | A | 7/1991 | Hodgkinson et al. |
| 5,043,991 | A | 8/1991 | Bradley |
| 5,053,171 | A | 10/1991 | Portney et al. |
| 5,095,487 | A | 3/1992 | Meyerhofer et al. |
| 5,098,426 | A | 3/1992 | Sklar et al. |
| 5,122,439 | A | 6/1992 | Miersch et al. |
| 5,132,996 | A | 7/1992 | Moore et al. |
| 5,146,088 | A | 9/1992 | Kingham et al. |
| 5,154,707 | A | 10/1992 | Rink et al. |
| 5,159,402 | A | 10/1992 | Ortiz, Jr. |
| 5,162,643 | A | 11/1992 | Currie |
| 5,166,818 | A | 11/1992 | Chase et al. |
| 5,187,759 | A | 2/1993 | DiGiovanni et al. |
| 5,194,713 | A | 3/1993 | Egitto et al. |
| 5,204,867 | A | 4/1993 | Koschmann |
| 5,206,455 | A | 4/1993 | Williams et al. |
| 5,217,003 | A | 6/1993 | Wilk |
| 5,237,576 | A | 8/1993 | DiGiovanni et al. |
| 5,255,117 | A | 10/1993 | Cushman |
| 5,265,107 | A | 11/1993 | Delfyett, Jr. |
| 5,267,077 | A | 11/1993 | Blonder |
| 5,278,853 | A | 1/1994 | Shirai et al. |
| 5,291,501 | A | 3/1994 | Hanna |
| 5,293,186 | A | 3/1994 | Seden et al. |
| 5,301,347 | A | 4/1994 | Kensky |
| 5,302,835 | A | 4/1994 | Bendett et al. |
| 5,313,262 | A | 5/1994 | Leonard |
| 5,315,431 | A | 5/1994 | Masuda et al. |
| 5,315,436 | A | 5/1994 | Lowenhar et al. |
| 5,329,398 | A | 7/1994 | Lai et al. |
| 5,331,131 | A | 7/1994 | Opdyke |
| 5,355,383 | A | 10/1994 | Lockard |
| 5,367,143 | A | 11/1994 | White, Jr. |
| 5,400,350 | A | 3/1995 | Galvanauskas |
| 5,409,376 | A | 4/1995 | Murphy |
| 5,411,918 | A | 5/1995 | Keible et al. |
| 5,414,725 | A | 5/1995 | Fermann et al. |
| 5,418,809 | A | 5/1995 | August, Jr. et al. |
| 5,428,471 | A | 6/1995 | McDermott |
| 5,430,572 | A | 7/1995 | DiGiovanni et al. |
| 5,440,573 | A | 8/1995 | Fermann |
| 5,446,813 | A | 8/1995 | Lee et al. |
| 5,450,427 | A | 9/1995 | Fermann et al. |
| 5,479,422 | A | 12/1995 | Fermann et al. |
| 5,489,984 | A | 2/1996 | Hariharan et al. |
| 5,493,579 | A | 2/1996 | Ressl et al. |
| 5,499,134 | A | 3/1996 | Galvanauskas et al. |
| 5,517,043 | A | 5/1996 | Ma et al. |
| 5,520,679 | A | 5/1996 | Lin |
| 5,548,098 | A | 8/1996 | Sugawara et al. |
| 5,572,335 | A | 11/1996 | Stevens |
| 5,572,358 | A | 11/1996 | Gabl et al. |
| 5,585,642 | A | 12/1996 | Britton et al. |
| 5,585,652 | A | 12/1996 | Kamasz et al. |
| 5,585,913 | A | 12/1996 | Hariharan et al. |
| 5,590,142 | A | 12/1996 | Shan |
| 5,592,327 | A | 1/1997 | Gabl et al. |
| 5,596,668 | A | 1/1997 | DiGiovanni et al. |
| 5,602,673 | A | 2/1997 | Swan |
| 5,602,677 | A | 2/1997 | Tournois |
| 5,615,043 | A | 3/1997 | Plaessmann et al. |
| 5,617,434 | A | 4/1997 | Tamura et al. |
| 5,624,587 | A | 4/1997 | Otsuki et al. |
| 5,625,544 | A | 4/1997 | Kowshik et al. |
| 5,627,848 | A | 5/1997 | Fermann et al. |
| 5,631,771 | A | 5/1997 | Swan |
| 5,633,750 | A | 5/1997 | Nogiwa et al. |
| 5,633,885 | A | 5/1997 | Galvanauskas et al. |
| 5,642,447 | A | 6/1997 | Pan et al. |
| 5,644,424 | A | 7/1997 | Backus et al. |
| 5,651,018 | A | 7/1997 | Mehuys et al. |
| 5,656,186 | A | 8/1997 | Mourou et al. |
| 5,657,153 | A | 8/1997 | Endriz et al. |
| 5,661,829 | A | 8/1997 | Zheng |
| 5,663,731 | A | 9/1997 | Theodoras, II et al. |
| 5,665,942 | A | 9/1997 | Williams et al. |
| 5,666,722 | A | 9/1997 | Tamm et al. |

(56) References Cited

U.S. PATENT DOCUMENTS

| | | |
|---|---|---|
| 5,670,067 A | 9/1997 | Koide et al. |
| 5,677,769 A | 10/1997 | Bendett |
| 5,689,361 A | 11/1997 | Damen et al. |
| 5,689,519 A | 11/1997 | Fermann et al. |
| 5,694,501 A | 12/1997 | Alavie et al. |
| 5,696,782 A | 12/1997 | Harter et al. |
| 5,701,319 A | 12/1997 | Fermann |
| 5,703,639 A | 12/1997 | Farrier et al. |
| 5,708,669 A | 1/1998 | DiGiovanni et al. |
| 5,710,424 A | 1/1998 | Thoedoras, II et al. |
| 5,720,894 A | 2/1998 | Neev et al. |
| 5,726,855 A | 3/1998 | Mourou et al. |
| 5,734,762 A | 3/1998 | Ho et al. |
| 5,736,709 A | 4/1998 | Neiheisel |
| 5,739,933 A | 4/1998 | Dembeck et al. |
| 5,770,864 A | 6/1998 | Dlugos |
| 5,771,253 A | 6/1998 | Chang-Hasnain et al. |
| 5,778,016 A | 7/1998 | Sucha et al. |
| 5,781,289 A | 7/1998 | Sabsabi et al. |
| 5,786,117 A | 7/1998 | Hoshi et al. |
| 5,790,574 A | 8/1998 | Rieger et al. |
| 5,815,519 A | 9/1998 | Aoshima et al. |
| 5,818,630 A | 10/1998 | Fermann et al. |
| 5,822,097 A | 10/1998 | Tournois |
| 5,844,149 A | 12/1998 | Akiyoshi et al. |
| 5,847,825 A | 12/1998 | Alexander |
| 5,847,863 A | 12/1998 | Galvanauskas et al. |
| 5,862,287 A | 1/1999 | Stock et al. |
| 5,862,845 A | 1/1999 | Chin et al. |
| 5,867,304 A | 2/1999 | Galvanauskas et al. |
| 5,875,408 A | 2/1999 | Bendett et al. |
| 5,880,823 A | 3/1999 | Lu |
| 5,880,877 A | 3/1999 | Fermann et al. |
| 5,898,485 A | 4/1999 | Nati, Jr. |
| 5,907,157 A | 5/1999 | Yoshioka et al. |
| 5,920,668 A | 7/1999 | Uehara et al. |
| 5,923,686 A | 7/1999 | Fermann et al. |
| 5,929,430 A | 7/1999 | Yao et al. |
| 5,936,716 A | 8/1999 | Pinsukanjana et al. |
| 5,994,667 A | 11/1999 | Merdan et al. |
| 5,999,847 A | 12/1999 | Elstrom |
| 6,014,249 A | 1/2000 | Fermann et al. |
| 6,016,452 A | 1/2000 | Kasevich |
| 6,020,591 A | 2/2000 | Harter et al. |
| 6,034,975 A | 3/2000 | Harter et al. |
| 6,041,020 A | 3/2000 | Caron et al. |
| 6,061,373 A | 5/2000 | Brockman et al. |
| 6,072,811 A | 6/2000 | Fermann et al. |
| 6,075,588 A | 6/2000 | Pinsukanjana et al. |
| 6,081,369 A | 6/2000 | Waarts et al. |
| 6,088,153 A | 7/2000 | Anthon et al. |
| 6,099,522 A | 8/2000 | Knopp et al. |
| 6,120,857 A | 9/2000 | Balooch et al. |
| 6,122,097 A | 9/2000 | Weston et al. |
| 6,130,780 A | 10/2000 | Joannopoulos et al. |
| 6,134,003 A | 10/2000 | Tearney et al. |
| 6,141,140 A | 10/2000 | Kim |
| 6,151,338 A | 11/2000 | Grubb et al. |
| 6,154,310 A | 11/2000 | Galvanauskas et al. |
| 6,156,030 A | 12/2000 | Neev |
| 6,161,543 A | 12/2000 | Cox et al. |
| 6,168,590 B1 * | 1/2001 | Neev ................................ 606/9 |
| 6,172,611 B1 | 1/2001 | Hussain et al. |
| 6,175,437 B1 | 1/2001 | Diels et al. |
| 6,179,421 B1 | 1/2001 | Pang |
| 6,181,463 B1 | 1/2001 | Galvanauskas et al. |
| 6,190,380 B1 | 2/2001 | Abela |
| 6,198,568 B1 | 3/2001 | Galvanauskas et al. |
| 6,198,766 B1 | 3/2001 | Schuppe et al. |
| 6,201,914 B1 | 3/2001 | Duguay et al. |
| 6,208,458 B1 | 3/2001 | Galvanauskas et al. |
| 6,228,748 B1 | 5/2001 | Anderson et al. |
| 6,246,816 B1 | 6/2001 | Moore et al. |
| 6,249,630 B1 | 6/2001 | Stock et al. |
| 6,252,892 B1 | 6/2001 | Jiang et al. |
| 6,256,328 B1 | 7/2001 | Delfyett et al. |
| 6,269,108 B1 | 7/2001 | Tabirian et al. |
| 6,271,650 B1 | 8/2001 | Massie et al. |
| 6,275,250 B1 | 8/2001 | Sanders et al. |
| 6,275,512 B1 | 8/2001 | Fermann |
| 6,281,471 B1 | 8/2001 | Smart |
| 6,290,910 B1 | 9/2001 | Chalk |
| 6,303,903 B1 | 10/2001 | Liu |
| 6,314,115 B1 | 11/2001 | Delfyett et al. |
| 6,325,792 B1 | 12/2001 | Swinger et al. |
| 6,327,074 B1 | 12/2001 | Bass et al. |
| 6,327,282 B2 | 12/2001 | Hammons et al. |
| 6,330,383 B1 | 12/2001 | Cai et al. |
| 6,334,011 B1 | 12/2001 | Galvanauskas et al. |
| 6,335,821 B1 | 1/2002 | Suzuki et al. |
| 6,340,806 B1 | 1/2002 | Smart et al. |
| RE37,585 E | 3/2002 | Mourou et al. |
| 6,355,908 B1 | 3/2002 | Tatah et al. |
| 6,359,681 B1 | 3/2002 | Housand et al. |
| 6,362,454 B1 | 3/2002 | Liu |
| 6,365,869 B1 | 4/2002 | Swain et al. |
| 6,366,395 B1 | 4/2002 | Drake et al. |
| 6,370,171 B1 | 4/2002 | Horn et al. |
| 6,370,422 B1 | 4/2002 | Richards-Kortum et al. |
| 6,371,469 B1 | 4/2002 | Gray |
| 6,396,317 B1 | 5/2002 | Roller et al. |
| 6,404,944 B1 | 6/2002 | Wa et al. |
| 6,407,363 B2 | 6/2002 | Dunsky et al. |
| 6,418,154 B1 | 7/2002 | Kneip et al. |
| 6,418,256 B1 | 7/2002 | Danziger et al. |
| 6,421,169 B1 | 7/2002 | Bonnedal et al. |
| 6,425,912 B1 | 7/2002 | Knowlton |
| 6,433,303 B1 | 8/2002 | Liu et al. |
| 6,433,305 B1 | 8/2002 | Liu et al. |
| 6,433,760 B1 | 8/2002 | Vaissie et al. |
| 6,437,283 B1 | 8/2002 | Wiggermann et al. |
| 6,463,314 B1 | 10/2002 | Haruna |
| 6,482,199 B1 | 11/2002 | Neev |
| 6,485,413 B1 | 11/2002 | Boppart et al. |
| 6,486,435 B1 | 11/2002 | Beyer et al. |
| 6,496,099 B2 | 12/2002 | Wang et al. |
| 6,501,590 B2 | 12/2002 | Bass et al. |
| 6,522,460 B2 | 2/2003 | Bonnedal et al. |
| 6,522,674 B1 | 2/2003 | Niwano et al. |
| 6,525,873 B2 | 2/2003 | Gerrish et al. |
| 6,526,085 B2 | 2/2003 | Vogler et al. |
| 6,526,327 B2 | 2/2003 | Kar et al. |
| 6,529,319 B2 | 3/2003 | Youn et al. |
| 6,541,731 B2 | 4/2003 | Mead et al. |
| 6,547,453 B1 | 4/2003 | Stummer et al. |
| 6,549,547 B2 | 4/2003 | Galvanauskas et al. |
| 6,552,301 B2 | 4/2003 | Herman et al. |
| 6,555,781 B2 | 4/2003 | Ngoi et al. |
| 6,556,733 B2 | 4/2003 | Dy et al. |
| 6,562,698 B2 | 5/2003 | Manor |
| 6,567,431 B2 | 5/2003 | Tabirian et al. |
| 6,570,704 B2 | 5/2003 | Palese |
| 6,573,813 B1 | 6/2003 | Joannopoulos et al. |
| 6,574,024 B1 | 6/2003 | Liu |
| 6,574,250 B2 | 6/2003 | Sun et al. |
| 6,576,917 B1 | 6/2003 | Silfvast |
| 6,580,553 B2 | 6/2003 | Kim et al. |
| 6,587,488 B1 | 7/2003 | Meissner et al. |
| 6,592,574 B1 | 7/2003 | Shimmick et al. |
| 6,597,497 B2 | 7/2003 | Wang et al. |
| 6,603,903 B1 | 8/2003 | Tong et al. |
| 6,603,911 B1 | 8/2003 | Fink et al. |
| 6,608,951 B1 | 8/2003 | Goldenberg et al. |
| 6,614,565 B1 | 9/2003 | Klug et al. |
| 6,621,040 B1 | 9/2003 | Perry et al. |
| 6,621,045 B1 | 9/2003 | Liu et al. |
| 6,627,421 B1 | 9/2003 | Unger et al. |
| 6,627,844 B2 | 9/2003 | Liu et al. |
| 6,642,477 B1 | 11/2003 | Patel et al. |
| 6,647,031 B2 | 11/2003 | Delfyett et al. |
| 6,654,161 B2 | 11/2003 | Bass et al. |
| 6,661,568 B2 | 12/2003 | Hollemann et al. |
| 6,661,816 B2 | 12/2003 | Delfyett et al. |
| 6,661,820 B1 | 12/2003 | Camilleri et al. |

(56) References Cited

U.S. PATENT DOCUMENTS

| | | | |
|---|---|---|---|
| 6,671,298 B1 | 12/2003 | Delfyett et al. |
| 6,677,552 B1 | 1/2004 | Tulloch et al. |
| 6,681,079 B1 | 1/2004 | Maroney |
| 6,690,686 B2 | 2/2004 | Delfyett et al. |
| 6,695,835 B2 | 2/2004 | Furuno et al. |
| 6,696,008 B2 | 2/2004 | Brandinger |
| 6,697,402 B2 | 2/2004 | Crawford |
| 6,697,408 B2 | 2/2004 | Kennedy et al. |
| 6,700,094 B1 | 3/2004 | Kuntze |
| 6,700,698 B1 | 3/2004 | Scott |
| 6,706,036 B2 | 3/2004 | Lai |
| 6,706,998 B2 | 3/2004 | Cutler |
| 6,710,288 B2 | 3/2004 | Liu et al. |
| 6,710,293 B2 | 3/2004 | Liu et al. |
| 6,711,334 B2 | 3/2004 | Szkopek et al. |
| 6,716,475 B1 | 4/2004 | Fink et al. |
| 6,720,519 B2 | 4/2004 | Liu et al. |
| 6,723,991 B1 | 4/2004 | Sucha et al. |
| 6,727,458 B2 | 4/2004 | Smart |
| 6,728,273 B2 | 4/2004 | Perry |
| 6,728,439 B2 | 4/2004 | Weisberg et al. |
| 6,735,229 B1 | 5/2004 | Delfyett et al. |
| 6,735,368 B2 | 5/2004 | Parker et al. |
| 6,738,144 B1 | 5/2004 | Dogariu |
| 6,738,408 B2 | 5/2004 | Abedin |
| 6,744,552 B2 | 6/2004 | Scalora et al. |
| 6,744,555 B2 | 6/2004 | Galvanauskas et al. |
| 6,749,285 B2 | 6/2004 | Liu et al. |
| 6,760,356 B2 | 7/2004 | Erbert et al. |
| 6,774,869 B2 | 8/2004 | Biocca et al. |
| 6,782,207 B1 | 8/2004 | Efimov |
| 6,787,734 B2 | 9/2004 | Liu |
| 6,788,864 B2 | 9/2004 | Ahmad et al. |
| 6,791,060 B2 | 9/2004 | Dunsky et al. |
| 6,791,071 B2 | 9/2004 | Woo et al. |
| 6,795,461 B1 | 9/2004 | Blair et al. |
| 6,801,550 B1 | 10/2004 | Snell et al. |
| 6,801,551 B1 | 10/2004 | Delfyett et al. |
| 6,801,557 B2 | 10/2004 | Liu |
| 6,803,539 B2 | 10/2004 | Liu et al. |
| 6,804,574 B2 | 10/2004 | Liu et al. |
| 6,807,353 B1 | 10/2004 | Fleming et al. |
| 6,807,375 B2 | 10/2004 | Dogariu |
| 6,815,638 B2 | 11/2004 | Liu |
| 6,819,694 B2 | 11/2004 | Jiang et al. |
| 6,819,702 B2 | 11/2004 | Sverdlov et al. |
| 6,819,837 B2 | 11/2004 | Li et al. |
| 6,822,187 B1 | 11/2004 | Hermann et al. |
| 6,822,251 B1 | 11/2004 | Arenberg et al. |
| 6,824,540 B1 | 11/2004 | Lin |
| 6,829,517 B2 | 12/2004 | Cheng et al. |
| 6,834,134 B2 | 12/2004 | Brennan, III et al. |
| 6,836,703 B2 | 12/2004 | Wang et al. |
| 6,878,900 B2 | 4/2005 | Corkum et al. |
| 6,882,772 B1 | 4/2005 | Lowery et al. |
| 6,885,683 B1 | 4/2005 | Fermann et al. |
| 6,887,804 B2 | 5/2005 | Sun et al. |
| 6,897,405 B2 | 5/2005 | Cheng et al. |
| 6,902,561 B2 | 6/2005 | Kurtz et al. |
| 6,915,040 B2 | 7/2005 | Willner et al. |
| 6,917,631 B2 | 7/2005 | Richardson et al. |
| 6,928,490 B1 | 8/2005 | Bucholz et al. |
| 6,937,629 B2 | 8/2005 | Perry et al. |
| 6,943,359 B2 | 9/2005 | Vardeny et al. |
| 6,956,680 B2 | 10/2005 | Morbieu et al. |
| 6,994,703 B2 | 2/2006 | Wang et al. |
| 7,001,373 B2 | 2/2006 | Clapham et al. |
| 7,002,733 B2 | 2/2006 | Dagenais et al. |
| 7,006,730 B2 | 2/2006 | Doerr |
| 7,022,119 B2 | 4/2006 | Hohla |
| 7,031,571 B2 | 4/2006 | Mihailov et al. |
| 7,068,408 B2 | 6/2006 | Sakai |
| 7,072,101 B2 | 7/2006 | Kapteyn et al. |
| 7,088,756 B2 | 8/2006 | Fermann et al. |
| 7,095,772 B1 | 8/2006 | Delfyett et al. |
| 7,097,640 B2 | 8/2006 | Wang et al. |
| 7,099,549 B2 | 8/2006 | Scheuer et al. |
| 7,116,688 B2 | 10/2006 | Sauter et al. |
| 7,132,289 B2 | 11/2006 | Kobayashi et al. |
| 7,143,769 B2 | 12/2006 | Stoltz et al. |
| 7,171,074 B2 | 1/2007 | DiGiovanni et al. |
| 7,217,266 B2 | 5/2007 | Anderson et al. |
| 7,220,255 B2 | 5/2007 | Lai |
| 7,233,607 B2 | 6/2007 | Richardson et al. |
| 7,257,302 B2 | 8/2007 | Fermann et al. |
| 7,321,605 B2 | 1/2008 | Albert |
| 7,321,713 B2 | 1/2008 | Akiyama et al. |
| 7,332,234 B2 | 2/2008 | Levinson et al. |
| 7,349,452 B2 | 3/2008 | Brennan, III et al. |
| 7,349,589 B2 | 3/2008 | Temelkuran et al. |
| 7,361,171 B2 | 4/2008 | Stoltz et al. |
| 7,367,969 B2 | 5/2008 | Stoltz et al. |
| 7,413,565 B2 | 8/2008 | Wang et al. |
| 7,414,780 B2 | 8/2008 | Fermann et al. |
| 7,444,049 B1 | 10/2008 | Kim et al. |
| 7,505,196 B2 | 3/2009 | Nati et al. |
| 7,518,788 B2 | 4/2009 | Fermann et al. |
| 7,584,756 B2 * | 9/2009 | Zadoyan et al. ............... 128/898 |
| 7,674,719 B2 | 3/2010 | Li et al. |
| 7,675,674 B2 | 3/2010 | Bullington et al. |
| 7,728,967 B2 | 6/2010 | Ochiai et al. |
| 7,751,118 B1 | 7/2010 | Di Teodoro et al. |
| 7,759,607 B2 | 7/2010 | Chism, II |
| 7,773,216 B2 | 8/2010 | Cheng et al. |
| 7,787,175 B1 | 8/2010 | Brennan, III et al. |
| 7,792,408 B2 | 9/2010 | Varming |
| 7,822,347 B1 | 10/2010 | Brennan, III et al. |
| 7,943,533 B2 | 5/2011 | Mizuno |
| 7,963,958 B2 | 6/2011 | Stoltz et al. |
| 7,998,404 B2 | 8/2011 | Huang et al. |
| RE43,605 E | 8/2012 | O'Brien et al. |
| 8,338,746 B2 | 12/2012 | Sun et al. |
| 8,373,090 B2 | 2/2013 | Gale et al. |
| 2001/0009250 A1 | 7/2001 | Herman et al. |
| 2001/0021294 A1 | 9/2001 | Cai et al. |
| 2001/0046243 A1 | 11/2001 | Schie |
| 2002/0003130 A1 | 1/2002 | Sun et al. |
| 2002/0051606 A1 | 5/2002 | Takushima et al. |
| 2002/0071454 A1 | 6/2002 | Lin |
| 2002/0091325 A1 | 7/2002 | Ostrovsky |
| 2002/0095142 A1 | 7/2002 | Ming |
| 2002/0097468 A1 | 7/2002 | Mecherle et al. |
| 2002/0097761 A1 | 7/2002 | Sucha et al. |
| 2002/0115273 A1 | 8/2002 | Chandra et al. |
| 2002/0118934 A1 | 8/2002 | Danziger et al. |
| 2002/0153500 A1 | 10/2002 | Fordahl et al. |
| 2002/0167581 A1 | 11/2002 | Cordingley et al. |
| 2002/0167974 A1 | 11/2002 | Kennedy et al. |
| 2002/0176676 A1 | 11/2002 | Johnson et al. |
| 2002/0186915 A1 | 12/2002 | Yu et al. |
| 2002/0191901 A1 | 12/2002 | Jensen |
| 2003/0011782 A1 | 1/2003 | Tanno |
| 2003/0031410 A1 | 2/2003 | Schnitzer |
| 2003/0039442 A1 | 2/2003 | Bond et al. |
| 2003/0053508 A1 | 3/2003 | Dane et al. |
| 2003/0055413 A1 | 3/2003 | Altshuler et al. |
| 2003/0060808 A1 | 3/2003 | Wilk |
| 2003/0086647 A1 | 5/2003 | Willner et al. |
| 2003/0095266 A1 | 5/2003 | Detalle et al. |
| 2003/0123496 A1 | 7/2003 | Broutin et al. |
| 2003/0142705 A1 | 7/2003 | Hackel et al. |
| 2003/0152115 A1 | 8/2003 | Jiang et al. |
| 2003/0156605 A1 | 8/2003 | Richardson et al. |
| 2003/0161365 A1 | 8/2003 | Perry et al. |
| 2003/0161378 A1 | 8/2003 | Zhang et al. |
| 2003/0178396 A1 | 9/2003 | Naumov et al. |
| 2003/0189959 A1 | 10/2003 | Erbert et al. |
| 2003/0202547 A1 | 10/2003 | Fermann et al. |
| 2003/0205561 A1 | 11/2003 | Iso |
| 2003/0214714 A1 | 11/2003 | Zheng |
| 2003/0223689 A1 | 12/2003 | Koch et al. |
| 2003/0235381 A1 | 12/2003 | Hunt |
| 2004/0000942 A1 | 1/2004 | Kapteyn et al. |
| 2004/0022695 A1 | 2/2004 | Simon et al. |

(56) References Cited

U.S. PATENT DOCUMENTS

| | | |
|---|---|---|
| 2004/0037505 A1 | 2/2004 | Morin |
| 2004/0042061 A1 | 3/2004 | Islam et al. |
| 2004/0049552 A1 | 3/2004 | Motoyama et al. |
| 2004/0101001 A1 | 5/2004 | Bergmann et al. |
| 2004/0128081 A1 | 7/2004 | Rabitz et al. |
| 2004/0134894 A1 | 7/2004 | Gu et al. |
| 2004/0134896 A1 | 7/2004 | Gu et al. |
| 2004/0160995 A1 | 8/2004 | Sauter et al. |
| 2004/0226922 A1 | 11/2004 | Flanagan |
| 2004/0226925 A1 | 11/2004 | Gu et al. |
| 2004/0231682 A1 | 11/2004 | Stoltz |
| 2004/0233944 A1 | 11/2004 | Dantus et al. |
| 2004/0263950 A1 | 12/2004 | Fermann et al. |
| 2005/0008044 A1 | 1/2005 | Fermann et al. |
| 2005/0018986 A1 | 1/2005 | Argyros et al. |
| 2005/0035097 A1 | 2/2005 | Stoltz |
| 2005/0036527 A1 | 2/2005 | Khazaei et al. |
| 2005/0038487 A1 | 2/2005 | Stoltz |
| 2005/0061779 A1 | 3/2005 | Blumenfeld et al. |
| 2005/0065502 A1 | 3/2005 | Stoltz |
| 2005/0067388 A1 | 3/2005 | Sun et al. |
| 2005/0074974 A1 | 4/2005 | Stoltz |
| 2005/0077275 A1 | 4/2005 | Stoltz |
| 2005/0105865 A1 | 5/2005 | Fermann et al. |
| 2005/0107773 A1 | 5/2005 | Bergt et al. |
| 2005/0111073 A1 | 5/2005 | Pan et al. |
| 2005/0127049 A1 | 6/2005 | Woeste et al. |
| 2005/0154380 A1 | 7/2005 | DeBenedictis et al. |
| 2005/0163426 A1 | 7/2005 | Fermann et al. |
| 2005/0167405 A1 | 8/2005 | Stoltz et al. |
| 2005/0171516 A1 | 8/2005 | Stoltz |
| 2005/0171518 A1 | 8/2005 | Stoltz et al. |
| 2005/0175280 A1 | 8/2005 | Nicholson |
| 2005/0177143 A1 | 8/2005 | Bullington et al. |
| 2005/0195726 A1 | 9/2005 | Bullington et al. |
| 2005/0213630 A1 | 9/2005 | Mielke et al. |
| 2005/0215985 A1 | 9/2005 | Mielke et al. |
| 2005/0218122 A1 | 10/2005 | Yamamoto et al. |
| 2005/0225846 A1 | 10/2005 | Nati et al. |
| 2005/0232560 A1 | 10/2005 | Knight et al. |
| 2005/0238070 A1 | 10/2005 | Imeshev et al. |
| 2005/0253482 A1 | 11/2005 | Kapps et al. |
| 2005/0259944 A1 | 11/2005 | Anderson et al. |
| 2005/0265407 A1 | 12/2005 | Braun et al. |
| 2005/0271094 A1 | 12/2005 | Miller et al. |
| 2005/0271340 A1 | 12/2005 | Weisberg et al. |
| 2005/0274702 A1 | 12/2005 | Deshi |
| 2006/0016891 A1 | 1/2006 | Giebel et al. |
| 2006/0030951 A1 | 2/2006 | Davlin et al. |
| 2006/0056480 A1 | 3/2006 | Mielke et al. |
| 2006/0064079 A1 | 3/2006 | Stoltz et al. |
| 2006/0067604 A1 | 3/2006 | Bull et al. |
| 2006/0084957 A1 | 4/2006 | Delfyett et al. |
| 2006/0120418 A1 | 6/2006 | Harter et al. |
| 2006/0126679 A1 | 6/2006 | Brennan et al. |
| 2006/0131288 A1 | 6/2006 | Sun et al. |
| 2006/0159137 A1 | 7/2006 | Shah |
| 2006/0187974 A1 | 8/2006 | Dantus |
| 2006/0209908 A1 | 9/2006 | Pedersen et al. |
| 2006/0210275 A1 | 9/2006 | Vaissie et al. |
| 2006/0221449 A1 | 10/2006 | Glebov et al. |
| 2006/0249816 A1 | 11/2006 | Li et al. |
| 2006/0250025 A1 | 11/2006 | Kitagawa et al. |
| 2006/0268949 A1 | 11/2006 | Gohle et al. |
| 2007/0025728 A1 | 2/2007 | Nakazawa et al. |
| 2007/0047965 A1 | 3/2007 | Liu et al. |
| 2007/0098025 A1 | 5/2007 | Hong et al. |
| 2007/0106416 A1 | 5/2007 | Griffiths et al. |
| 2007/0196048 A1 | 8/2007 | Galvanauskas et al. |
| 2007/0229939 A1 | 10/2007 | Brown et al. |
| 2007/0253455 A1 | 11/2007 | Stadler et al. |
| 2007/0273960 A1 | 11/2007 | Fermann et al. |
| 2008/0050078 A1 | 2/2008 | Digonnet et al. |
| 2008/0058781 A1 | 3/2008 | Langeweyde et al. |
| 2008/0232407 A1 | 9/2008 | Harter et al. |
| 2008/0240184 A1 | 10/2008 | Cho et al. |
| 2009/0020511 A1 | 1/2009 | Kommera et al. |
| 2009/0244695 A1 | 10/2009 | Marcinkevicius et al. |
| 2009/0245302 A1 | 10/2009 | Baird et al. |
| 2009/0257464 A1 | 10/2009 | Dantus et al. |
| 2009/0273828 A1 | 11/2009 | Waarts et al. |
| 2009/0290151 A1 | 11/2009 | Agrawal et al. |
| 2009/0297155 A1 | 12/2009 | Weiner et al. |
| 2010/0013036 A1 | 1/2010 | Carey |
| 2010/0040095 A1 | 2/2010 | Mielke et al. |
| 2010/0118899 A1 | 5/2010 | Peng et al. |
| 2010/0157418 A1 | 6/2010 | Dong et al. |
| 2010/0181284 A1 | 7/2010 | Lee et al. |
| 2010/0276405 A1 | 11/2010 | Cho et al. |
| 2011/0069723 A1 | 3/2011 | Dong et al. |
| 2014/0044139 A1 | 2/2014 | Dong et al. |
| 2014/0140361 A1 | 5/2014 | Jiang |

FOREIGN PATENT DOCUMENTS

| | | |
|---|---|---|
| EP | 1462831 A1 | 9/2004 |
| JP | 8171103 | 7/1996 |
| JP | 11189472 A | 7/1999 |
| JP | 2003181661 A | 7/2003 |
| JP | 2003344883 | 12/2003 |
| WO | WO 9428972 A1 | 12/1994 |
| WO | WO 2004/105100 A2 | 12/2004 |
| WO | WO 2004/114473 A2 | 12/2004 |
| WO | WO 2005/018060 A2 | 2/2005 |
| WO | WO 2005/018061 A2 | 2/2005 |
| WO | WO 2005/018062 A2 | 2/2005 |
| WO | WO 2005/018063 A2 | 2/2005 |
| WO | WO2007034317 | 3/2007 |

OTHER PUBLICATIONS

Engeness et al., "Dispersion Tailoring and Compensation by Modal Interations in Omniguide Fibers," Optics Express, May 19, 2003, pp. 1175-1196, vol. 11, No. 10.

Fink et al., "Guiding Optical Light in Air Using an All-Dielectric Structure," Journal of Lightwave Technology, Nov. 1999, pp. 2039-2041, vol. 17, No. 11.

Siegman, "Unstable Optical Resonators", Applied Optics, Feb. 1974, pp. 353-367, vol. 13, No. 2.

Koechner, "Solid State Laser Engineering", Oct. 29, 1999, Section 5.5, pp. 270-277, 5th Edition, Springer.

Chen et al. "Dispersion-Managed Mode Locking", Journal of the Optical Society of America B, Nov. 1999, pp. 1999-2004, vol. 16, No. 11, Optical Society of America.

Resan et al. "Dispersion-Managed Semiconductor Mode-Locked Ring Laser", Optics Letters, Aug. 1, 2003, pp. 1371-1373, vol. 28, No. 15, Optical Society of America.

Dasgupta, S. et al., "Design of Dispersion-Compensating Bragg Fiber with an Ultrahigh Figure of Merit," Optics Letters, Aug. 1, 2005, vol. 30, No. 15, Optical Society of America.

Mohammed, W. et al., "Selective Excitation of the TE01 Mode in Hollow-Glass Waveguide Using a Subwavelength Grating," IEEE Photonics Technology Letters, Jul. 2005, vol. 17, No. 7, IEEE.

Delfyett, P et al., "Ultrafast Semiconductor Laser-Diode-Seeded Cr:LiSAF Rengerative Amplifier System", Applied Optics, May 20, 1997, pp. 3375-3380, vol. 36, No. 15, Octoical Society of America.

Levy et al., "Engineering Space-Variant INhomogeneous Media for Polarization Control," Optics Letters, Aug. 1, 2004, pp. 1718-1720, vol. 29, No. 15, Optical Society of America.

Ibanescu et al., "Analysis of Mode Structure in Hollow Dielectric Waveguide Fibers," Physical Review E 67, 2003, The American Physical Society.

Nishimura et al., "In Vivo Manipulation of Biological Systems with Femtosecond Laser Pulses," Proc. SPIE 6261, 62611J, pp. 1-10, 2006.

Stevenson et al., Femtosecond Optical Transfection of Cells: Viability and Efficiency, Optics Express, vol. 14, No. 16, pp. 7125-7133, Aug. 7, 2006.

Tirlapur et al., "Targeted Transfection by Femtosecond Laser," Nature Publishing Group, vol. 418, pp. 290-291, Jul. 18, 2002.

(56) References Cited

OTHER PUBLICATIONS

Tsai et al., "Ultrashort Pulsed Laser Light," Optics & Photonics News, pp. 25-29, Jul. 2004.
Vaissie et al., "Desktop Ultra-Short Pulse Laser at 1552 nm,"Ultrashort Pulse Laser Materials Interaction Workshop (Raydiance)—Directed Energy Professional Society (DEPS), Sep. 28, 2006.
Stock et al., "Chirped Pulse Amplification in an Erbium-doped Diber Oscillator/Erbium-doped Fiber Amplifier System", Optics Communications, North-Holland Publishing Co., Amsterdam, NL, vol. 106, No. 4/5/06, Mar. 15, 1994, pp. 249-252, XP000429901, ISSN: 0030-4018.
Strickland et al., "Compression of Amplified Chirped Optical Pulses", Optics Communications, North-Holland Publishing Co., Amersterdam, NL, vol. 56, No. 3, Dec. 1, 1985, pp. 219-221, XP024444933 ISSN: 0030-4018 (retrieved on Dec. 11, 1985.
Temelkuran, B. et al., "Wavelength-scalable Hollow Optical Fibres with Large Photonic Bandgaps for CO2 Laser Transmission," Nature, Dec. 12, 2002, pp. 650-653.
Thurston, R.N. et al., "Analysis of Picosecond Pulse Shape Synthesis by Spectral Masking in a Grating Pulse Compressor," IEEE Journal of Quantum Electronics, vol. EQ-22, No. 5, pp. 682-696, May 1986.
Weiner, A.M. et al., "Synthesis of Phase-coherent, Picosecond Optical Square Pulses," Optics Letters, vol. 11, No. 3, pp. 153-155, Mar. 1986.
Weiner, A.M., "Femtosecond Optical Pulse Shaping and Processing," Prog. Quant. Electr. 1995, vol. 19, pp. 161-237, 1995.
Weiner, A.M., "High-resolution femtosecond Pulse Shaping," Journal of the Optical Society of America B. vol. 5, No. 8, pp. 1563-1572, Aug. 1988.
Wells, D.J., "Gene Therapy Progress and Prospects: electroporation and Other Physical Methods," Gene Therapy, Nature Publishing Group, vol. 11, pp. 1363-1369, Aug. 5, 2004, (http://www.nature.com/gt).
White, W.E., et al., "Compensation of Higher-order Frequency-dependent Phase Terms in Chirped-pulse Amplification Systems," Optics Letters, vol. 18, No. 16, pp. 1343-1345, Aug. 15, 1993.
Yamakawa et al., "1 Hz, 1 ps, terawatt Nd: glass laser", Optics Communications, North-Holland Publishing Co. Amsterdam, NL, vol. 112, No. 1-2, Nov. 1, 1994, pp. 37-42, XP024424285.
Yan et al., Ultrashort Pulse Measurement Using Interferometric Autocorrelator Based on Two-photon-absorbtion Detector at 1.55μm Wavelength Region., 2005, Proceedings of SPIE vol. 5633, Advanced Materials and Devices for Sensing and Imaging II, pp. 424-429.
Yi, Y. et al., "Sharp Bending of On-Chip silicon Bragg Cladding Waveguide With Light Guiding on Low Index Core Materials", IEEE Journal of Selected Topics in Quantum Electronics, vol. 12, No. 6, Nov./Dec. 2006, pp. 1345-1348.
Yi, Y., et al., "On-chip Si-based Bragg Cladding Waveguide with High Index Contrast Bilayers", Optics Express, vol. 12, No. 20, Oct. 4, 2004, pp. 4775-4780.
Yin, D. et al., "Integrated ARROW Waveguides with Hollow Cores", Optics Express, vol. 12, No. 12, Jun. 14, 2004, pp. 2710-2715.
Zhou, S. et al., "Compensation of nonlinear Phase Shifts with Third-order Dispersion in Short-pulse Fiber Amplifiers," Optics Express, vol. 13, No. 13, pp. 4869-2877, Jun. 27, 2005.
Agostinelli, J. et al., "Optical Pulse Shaping with a Grating Pair," Applied Optics, vol. 18, No. 14, pp. 2500-2504, Jul. 15, 1979.
Anastassiou et al., "Photonic Bandgap Fibers Exploiting Omnidirectional Reflectivity Enable Flexible Delivery of Infrared Lasers for Tissue Cutting," Proceedings of the SPIE—the International Society for Optical Engineering, SPIE, US, vol. 5317, No. 1, Jan. 1, 2004, pp. 29-38, XP002425586 ISSN: 0277-786X.
Benoit, G. et al., "Dynamic All-optical Tuning of Transverse Resonant Cavity Modes in Photonic Bandgap Fibers, "Optics Letters, vol. 30, No. 13, Jul. 1, 2005, pp. 1620-1622.
Chen, L. et al., "Ultrashort Optical Pulse Interaction with Fibre Gratings and Device Applications," 1997, Canaga, located at http://www.collectionscanada.ca/obj/s4/f2/dsk2/ftp04/mq29402.pfd.

Chen, X. et al., "Highly Birefringent Hollow-core Photonic Bandgap Fiber," Optics Express, vol. 12, No. 16, Aug. 9, 2004, pp. 3888-3893.
De Matos et al., "Multi-kilowatt, Picosecond Pulses from an All-fiber Chirped Pulse Amplification System Using Air-core Photonic Bandgalp Fiber", Lasers and Electro-optics, 2004, (CLEO), Conference on San Francisco, CA USA, May 20-21, 2004, Piscataway, NJ, USA, IEEE, vol. May 17, 2004, pp. 973-974, XP010745448 ISBN: 978-1-55752-777-6.
De Matos, C.J.S. et al., "All-fiber Chirped Pulse Amplification using Highly-dispersive Air-core Photonic Bandgap Fiber," Nov. 3, 2003, Optics Express, pp. 2832-2837, vol. 11, No. 22.
Eggleton, et al., "Electrically Tunable Power Efficient Dispersion Compensating Fiber Bragg Grating," IEEE Photonics Technology Letters, vol. 11, No. 7, pp. 854-856, Jul. 1999.
Folkenberg, J.R., et al., "Broadband Single-polarization Photonic Crystal Fiber," Optics Letters, vol. 30, No. 12, Jun. 15, 2005, pp. 1446-1448.
Folkenberg, J.R., et al., "Polarization Maintaining Large Mode Area Photonic Crystal Fiber," Optics Express vol. 12, No. 5, Mar. 8, 2004, pp. 956-960.
Futami, F., et al., "Wideband Fibre Dispersion Equalisation up to Fourth-order for Long-distance Sub-picosecond Optical Pulse Transmission," Electronics Letters, vol. 35, No. 25, Dec. 9, 1999.
Galvanauskas, A. et al., "Chirped-pulse-amplification Circuits for Fiber Amplifiers, Based on Chirped-period Quasi-phase, matching gratings", Optics Letters, Nov. 1, 1998, p. 1695-1697, vol. 23, No. 21, Optical Society of America.
Hartl et al., "In-line high energy Yb Fiber Laser Based Chirped Pulse Amplifier System", Laser and Electro-Optics, 2004, (CLEO) Conference of San Francisco, CA USA May 20-21, 2004, Piscataway, NJ, USA, IEEE, vol. 1, May 17, 2004, pp. 563-565, XP010745382, ISBN: 978-1-55752-7777.
Hellstrom, E. et al., "Third-order Dispersion Compensation Using a Phase Modulator", Journal of Lightwave Technology, vol. 21, No. 5, pp. 1188-1197, May 2003.
Heritage, J. P. et al., "Picosecond Pulse Shaping by Spectral Phase and Amplitude Manipulation," Optics Letters, vol. 10, No. 12, pp. 609-611, Dec. 1985.
Heritage, J.P. et al., "Spectral Windowing of Frequency-Modulated Optical Pulses in a Grating Compressor," Applied Physics Letters, vol. 47, No. 2, pp. 87-89, Jul. 15, 1985.
Hill, K. et al., "Fiber Bragg Grating Technology Fundamentals and Overview," Journal of Lightwave Technology, Aug. 1997, vol. 15, No. 8, pp. 1263-1276.
Jiang, et al., "Fully Dispersion Compensated ~500 fs Pulse Transmission Over 50 km Single Mode Fiber," Optics Letters, vol. 30, No. 12, pp. 1449-1451, Jun. 15, 2005.
Jiang, et al., "Fully Dispersion Compensated ~500 fs Pulse Transmission Over 50 km Single Mode Fiber," Purdue University ECE Annual Research Summary, Jul. 1, 2004-Jun. 30, 2005.
Killey, et al., "Electronic Dispersion Compensation by Signal Predistortion Using Digital Processing and a Dual-Drive Mach-Zehnder Modulator," IEEE Photonics Technology Letters, vol. 17, No. 3, pp. 714-716, Mar. 2005.
Kim, K. et al., "1.4kW High Peak Power Generation from an All Semiconductor Mode-locked Master Oscillator Power Amplifier System Based on eXtreme Chirped Pulse Amplification (X-CPA)", Optics Express, Jun. 2, 2005, pp. 4600-4606, vol. 13, No. 12.
Kwon, et al., "Tunable Dispersion Slope Compensator Using a Chirped Fiber Bragg Grating Tuned by a Fan-shaped Thin Metallic Heat Channel," IEEE Photonics Technology Letters, vol. 18, No. 1, pp. 118-120, Jan. 1, 2006.
Kyungbum, Kim et al., "1.4kW High Peak Power Generation from an all Semiconductor Mode-locked Master Oscillator Power Amplifier System Based on eXtreme Chirped Pulse Amplification (X-CPA)", Optics Express, Jun. 2, 2005, pp. 4600-4606, vol. 13, No. 12.
Liao, K. et al.., "Large-aperture Chirped Volume Bragg Grating Based Fiber CPA System," Optics Express, Apr. 16, 2007, vol. 15, No. 8, pp. 4876-4882.
Lo, S. et al., "Semiconductor Hollow Optical Waveguides Formed by Omni-directional Reflectors", Optics Express, vol. 12, No. 26, Dec. 27, 2004, pp. 6589-6593.

(56) References Cited

OTHER PUBLICATIONS

Malinowski A. et al., "Short Pulse High Power Fiber Laser Systems," Proceedings of the 2005 Conference on Lasers and Electro-Optics (CLEO), Paper No. CThG3, pp. 1647-1649, May 26, 2005.

Mehier-Humbert, S. et al., "Physical Methods for Gene Transfer: Improving the Kinetics of Gene Delivery Into Cells," Advanced Drug Delivery Reviews, vol. 57, pp. 733-753, 2005.

Nibbering, E.T.J., et al. "Spectral Determination of the Amplitude and the Phase of Intense Ultrashort Optical Pulses," Journal Optical Society of America B, vol. 13, No. 2, pp. 317-329, Feb. 1996.

Nicholson, J. et al., "Propagation of Femotsecond Pulses in Large-mode-area, Higher-order-mode Fiber," Optics Letters, vol. 31, No. 21, 2005, pp. 3191-3193.

Noda, J. et al., "Polarization-maintaining Fibers and Their Applications", Journal of Lightwave Technology, vol. Lt-4, No. 8 Aug. 1986, pp. 1071-1089.

Palfrey et al., "Generation of 16-FSEC Frequency-tunable Pulses by Optical Pulse compression" Optics Letters, OSA, Optical Society of america, Washington, DC, USA, vol. 10, No. 11, Nov. 1, 1985, pp. 562-564, XP000710358 ISSN: 0146-9592.

Pelusi, M. D., et al., "Electrooptic Phase Modulation of Stretched 250-fs Pulses for Suppression of Third-Order Fiber Disperson in Transmission," IEEE Photonics Technology Letters, vol. 11, No. 11, pp. 1461-1463, Nov. 1999.

Pelusi, M. D., et al., "Phase Modulation of Stretched Optical Pulses for Suppression of Third-order Dispersion Effects in fibre Transmission," Electronics Letters, vol. 34, No. 17, pp. 1675-1677, Aug. 20, 1998.

Price et al., "Advances in High Power, Short Pulse, Fiber Laser Systems and Technology", Proceedings of SPIE—vol. 5709, Fiber Lasers II: Technology, Systems, and Applications, Apr. 2005, pp. 184-192.

Price et al., "Advances in High Power, Short Pulse, Fiber Laser Systems and Technology", Photonics West 2005, San Jose, California, Jan. 2005, pp. 5709-3720.

Ramachandran, S., et al., "High-power Amplification in a 2040-µm2 Higher Order Mode," SPIE Photonics West 2007, Post-deadline.

Schreiber, T., et al., "Design and High Power Operation of a Stress-induced single Polarization Single-transverse Mode LMA Yb-doped Photonic Crystal Fiber," Fiber Lasers III: Technology, Systems, and Applications, Andrew J.W. Brown, Johan Nilsson, Donald J. Harter, Andreas Tünnermann, eds., Proc. of SPIE, vol. 6102, pp. 61020C-1-61020C-9, 2006.

Schreiber, T., et al., "Stress-induced Single-polarization Single-transverse Mode Photonic Crystal Fiber with Low Nonlinearity," Optics Express, vol. 13, No. 19, Sep. 19, 2005, pp. 7621-7630.

Limpert et al., "All Fiber Chiped-Pulse Amplification System Based on Compression in Air-Guiding Photonic Bandgap Fiber", Optics Express, Dec. 1, 2003, vol. 11, No. 24, pp. 3332-3337.

* cited by examiner

LASER ABLATION METHOD AND APPARATUS HAVING A FEEDBACK LOOP AND CONTROL UNIT

CROSS-REFERENCE TO RELATED APPLICATIONS

This application is a continuation-in-part of U.S. patent application Ser. No. 10/849,585, published as U.S. Patent Application No. 2004/0231682, filed May 19, 2004, entitled "Scanned Small Spot Ablation with a High-Repetition-Rate Technical Field of the Invention"; a continuation-in-part of U.S. patent application Ser. No. 10/916,367, issued as U.S. Pat. No. 7,143,769, filed Aug. 11, 2004, entitled "Controlling Pulse Energy of an Optical Amplifier by Controlling Pump Diode Current"; a continuation-in-part of U.S. patent application Ser. No. 10/916,368, filed Aug. 11, 2004, entitled "Pulse Energy Adjustment for Changes in Ablation Spot Size"; a continuation-in-part of U.S. patent application Ser. No. 10/916,365, issued as U.S. Pat. No. 7,367,969, filed Aug. 11, 2004, entitled "Ablative Material Removal with a Preset Removal Rate or Volume or Depth"; a continuation-in-part of U.S. patent application Ser. No. 10/850,325, published as U.S. Patent Application No. 2005/0038487, filed May 19, 2004, entitled "Controlling Pulse Energy of an Optical Amplifier by Controlling Pump Diode Current"; a continuation-in-part of U.S. patent application Ser. No. 10/849,586, published as U.S. Patent Application No. 2005/0035097, filed May 19, 2004, entitled "Altering the Emission of an Ablation Beam for Safety or Control"; and a continuation-in-part of U.S. patent application Ser. No. 10/849,587, published as U.S. Patent Application No. 2005/0065502, filed May 19, 2004, entitled "Enabling or Blocking the Emission of an Ablation Beam Based on Color of Target Area", which applications claim benefits of earlier filing dates of U.S. Provisional Patent Application Ser. No. 60/494,275, filed Aug. 11, 2003, entitled "Controlling Pulse Energy of a Fiber Amplifier by Controlling Pump Diode Current"; Ser. No. 60/494,274, filed Aug. 11, 2003, entitled "Pulse Energy Adjustment for Changes in Ablation Spot Size"; Ser. No. 60/494,273, filed Aug. 11, 2003, entitled "Ablative Material Removal with a Preset Removal Rate or Volume or Depth"; Ser. No. 60/494,322, filed Aug. 11, 2003, entitled "Controlling Temperature of a Fiber Amplifier by Controlling Pump Diode Current"; Ser. No. 60/494,267, filed Aug. 11, 2003, entitled "Altering the Emission an Ablation Beam for Safety or Control"; Ser. No. 60/494,172, filed Aug. 11, 2003, entitled "Enabling or Blocking the Emission of an Ablation Beam Based on Color of Target Area"; and Ser. No. 60/503,578, filed Sep. 17, 2003, entitled "Controlling Optically-Pumped Optical Pulse Amplifiers", the contents of which applications are incorporated herein by reference.

BACKGROUND

1. Field of the Invention

The present invention relates generally to laser ablation systems and methods for ablative material removal, including but not limited to such applications as surgical laser ablation for medical purposes.

2. Description of the Prior Art

Laser has been used to remove or otherwise manipulate materials in a variety of ways. Laser can ablatively remove a material by disassociating the surface atoms. The process is generally referred to as "laser ablation." Practical applications of laser ablation commonly use pulsed laser, and more commonly use short laser pulses. More recently, lasers of ultrashort pulses have started to have applications. While definitions vary, in general "ultrashort" refers to optical pulses of duration less than approximately 10 picoseconds including femtosecond laser pulses, and this definition is used herein. These latest lasers promise superior performance and ease of application. In particular, ultrashort laser pulses are more effective in overcoming common thermal damage problems associated with older lasers. Numerous applications of ultrashort pulses have been developed that would be otherwise impossible or impractical to implement with other technologies. With ultrashort pulses, researchers have investigated many highly nonlinear processes in atomic, molecular, plasma, and solid-state physics, and accessed previously unexplored states of matter.

Ablative material removal is especially useful for medical purposes, as it is essentially non-thermal and generally painless. In the past 20 years, laser ablation has become an increasingly important tool for medical surgery, applied in cases that have grown to include open, endoscopic or laparoscopic soft tissue incision or removal, such as eye surgeries, laser ablation of the prostate, breast biopsy, cytoreduction for metastatic disease, decubitus or statis ulcers, hemorrhoidectomy, laparoscopic surgery; mastectomy, reduction mammoplasty. Endovenous laser ablation has also become a safe and highly effective treatment for varicose veins.

In addition to the advancements in the laser technology itself, laser ablation is further benefited from other supplemental means such as computer-aided positioning technology for precision operation.

Given the importance of laser ablation, it is desirable to develop a new laser ablation system that offers better controllability, more automation, and higher accuracy.

SUMMARY OF THE INVENTION

This invention improves the existing laser ablation systems and methods by providing a feedback mechanism that measures an indicative property of an ablation target or an indicative property of the pulsed laser projected on the ablation target. The feedback mechanism generates a feedback signal according to the measured indicative property, and sends the feedback signal to a control unit. The control unit then adjusts an output parameter of the pulsed laser according to the feedback signal to optimize ablation effect.

The indicative property is characteristic of either the ablation target or the pulsed laser that has been projected on the ablation target, or a combination thereof. In some embodiments, the indicative property is measured using an optical probe, such as a camera. In one embodiment, the indicative property is indicative of the size of a laser beam spot projected on the ablation target for ablation. For instance, the indicative property may comprise a diameter of the laser beam spot projected on the ablation target. In such an embodiment, the feedback signal may be determined according to a pulse energy density which is defined as pulse energy per unit area and obtained by calculating the ratio between pulse energy and the size of the laser beam spot.

An exemplary way to adjust the output parameter of the pulsed laser is changing pulse energy. In the above exemplary embodiment, for example, a feedback signal for increasing the pulse energy is generated if the pulse energy density of the pulsed laser is lower than a predetermined threshold or optimal level, and a feedback signal for decreasing the pulse energy is generated if the pulse energy density of the pulsed laser is higher than the predetermined threshold or optimal level.

In one embodiment, changing pulse energy is accomplished by changing a pump current of a pump diode pumping the laser device.

Alternatively, the output parameter of the pulsed laser may be adjusted by changing pulse rate (or pulse repetition rate) of the pulsed laser. In some embodiments, the pulse rate of the pulsed laser is adjusted by selecting a subset of pulses from a pulse train generated by the laser device.

In some embodiments, the indicative property being measured is a material composition of the ablation target. The material composition may be measured by sampling an ablation plume. In one embodiment, the material composition is measured by a Laser Induced Breakdown Spectroscopy (LIBS).

In the above embodiments, a threshold pulse energy density or an optimal pulse energy density according to the material composition of the ablation target may be pre-determined for the feedback purpose. The pulse energy may be then adjusted such that a resultant pulse energy density of the projected pulsed laser on the ablation target matches the threshold pulse energy density or the optimal pulse energy density predetermined according to the material composition of the ablation target.

In some embodiments, the indicative property being measured is indicative of progress of an ablation process on the ablation target. Accordingly, the output parameter of the pulsed laser may be adjusted by either changing pulse energy or changing pulse rate. For example, pulse energy may be increased if the indicative property indicates that no substantial ablation is taking place, and pulse rate may be adjusted if the indicative property indicates an ablation rate deviating from a desired material removal rate.

Measuring the indicative property and adjusting the output parameter of the pulsed laser may be performed dynamically during the ablation process.

The present invention also provides an apparatus for laser ablation. The apparatus has a laser device for generating a pulsed laser and projecting the pulsed laser onto an ablation target to be ablated. The apparatus also has a probe for measuring an indicative property of the ablation target or an indicative property of the pulsed laser projected on the ablation target. The apparatus further has a control loop for generating a feedback signal according to the measured indicative property, sending the feedback signal to a control unit, and adjusting an output parameter of the pulsed laser according to the feedback signal to optimize ablation effect. The probe may be an optical sensor adapted for measuring a size of the laser beam spot projected on the ablation target.

In one embodiment, the control loop may be adapted for changing pulse energy by changing a pump current of a pump diode pumping the laser device. The control loop may also be adapted for changing pulse rate of the pulsed laser by, for example, selecting a subset of pulses from a pulse train generated by the laser device.

The probe may be a camera, a video camera, an infrared camera, a UV camera, a vidicon camera, a television camera remote to the ablation target, or an in vivo camera. The probe may comprise a spectroscopy unit, such as a Laser Induced Breakdown Spectroscopy (LIBS), to detect a material composition of the ablation target.

For some applications, the pulsed laser desirably has short pulses. Some embodiments, for example, have a pulse duration shorter than 1 picosecond, or a pulse duration shorter than 100 femtoseconds. For some applications, the pulse energy density of the pulsed laser ranges from about 0.1 Joules/cm2 to about 20 Joules/cm2.

The present invention improves the controllability and precision of laser ablation by using a feedback loop monitoring the ablation target that is being ablated. This invention can be used for various types of laser ablation, particularly for use as a medical surgical tool.

Other features and advantages of the invention will become more readily understandable from the following detailed description and figures.

BRIEF DESCRIPTION OF THE FIGURES

The invention will be described in detail along with the following figures, in which like parts are denoted with like reference numerals or letters.

DETAILED DESCRIPTION OF THE INVENTION

Figure 1:
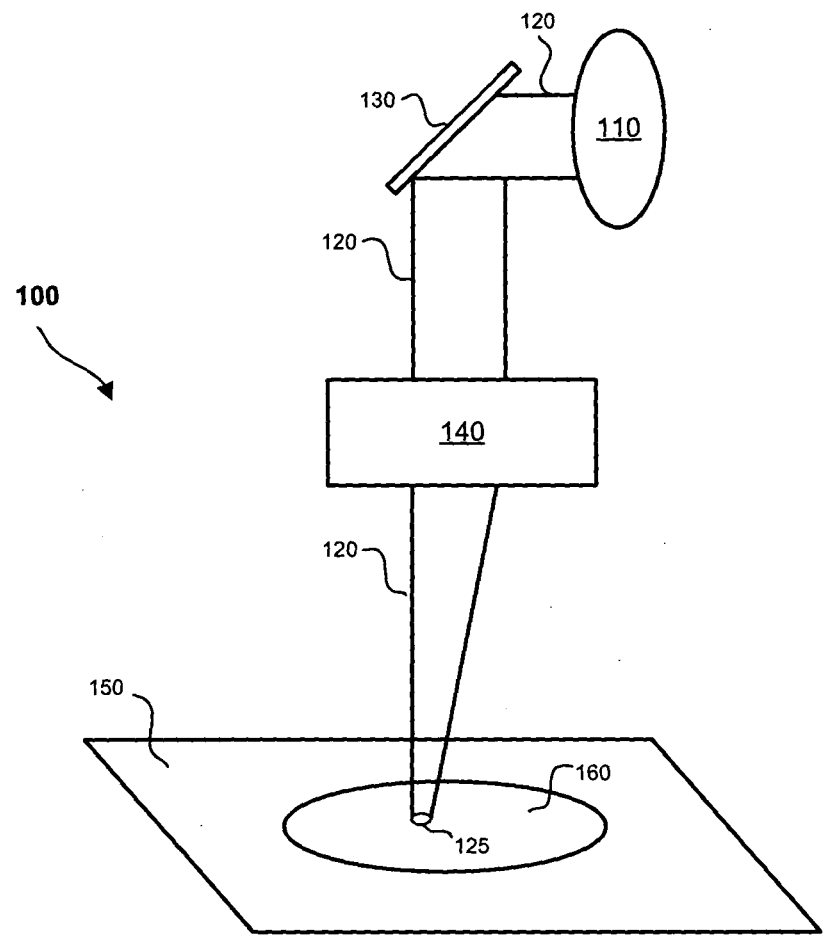
FIG. 1 is a schematic illustration of a conventional laser ablation system.

FIG. 1 is a schematic illustration of a conventional laser ablation system. Laser ablation system 100 has laser device 110 for generating laser beam 120, which is reflected by mirror 130, processed by an optical device 140 (typically a lens system) and focused on ablation target 150. The focused laser beam 120 projects laser spot 125 in ablation field 160, which is a part of ablation target 150 intended to be ablated. For a given ablation spot, laser ablation process uses the focused laser beam 120 to remove a surface material on the small spot where the laser beam 120 is projected and focused on to form laser spot 125.

The ablation point and depth are controlled via moving mirror 130, which is typically done through a galvanometer (not shown), a device for detecting or measuring a small electric current by movements of a magnetic needle or of a coil in a magnetic field. Commercial galvanometers are available which use an electric current through a coil to induce precise movements of optical devices, such as mirror 130 in FIG. 1. Because generally the ablation field 160 that needs to be ablated is much greater than the spot size of the laser spot 125, a scanning mechanism (not shown) is used to scan ablation field 160 by systematically moving laser beam 120 and the associated laser spot 125 across ablation field 160.

To carry out the process of scanning, a coordination system is required to position the focused laser spot 125 on ablation field 160 and dynamically and systematically move the focused laser beam 120 and the projected laser spot 125 across ablation field 160 on the target 150. Some laser ablation applications may contain a sophisticated coordination system for positioning the laser beam 120 and the associated laser spot 125 automatically and precisely.

Positioning the laser beam 120 and the associated laser spot 125, however, is not the only important factor involved in laser ablation. The present invention improves the existing laser ablation systems and methods by taking into consideration several other factors involved in the laser ablation process, particularly in the scanning process. In addition to positioning the laser spot on the target, laser ablation including the process of scanning should ideally be performed in a manner that is, on the one hand, as speedy as possible, but on the other hand, ensures that proper laser ablation has taken effect during scanning. With respect to these requirements, conventional laser ablation methods and systems generally lack sophistication in terms of controllability, automation, and precision.

Figure 2:
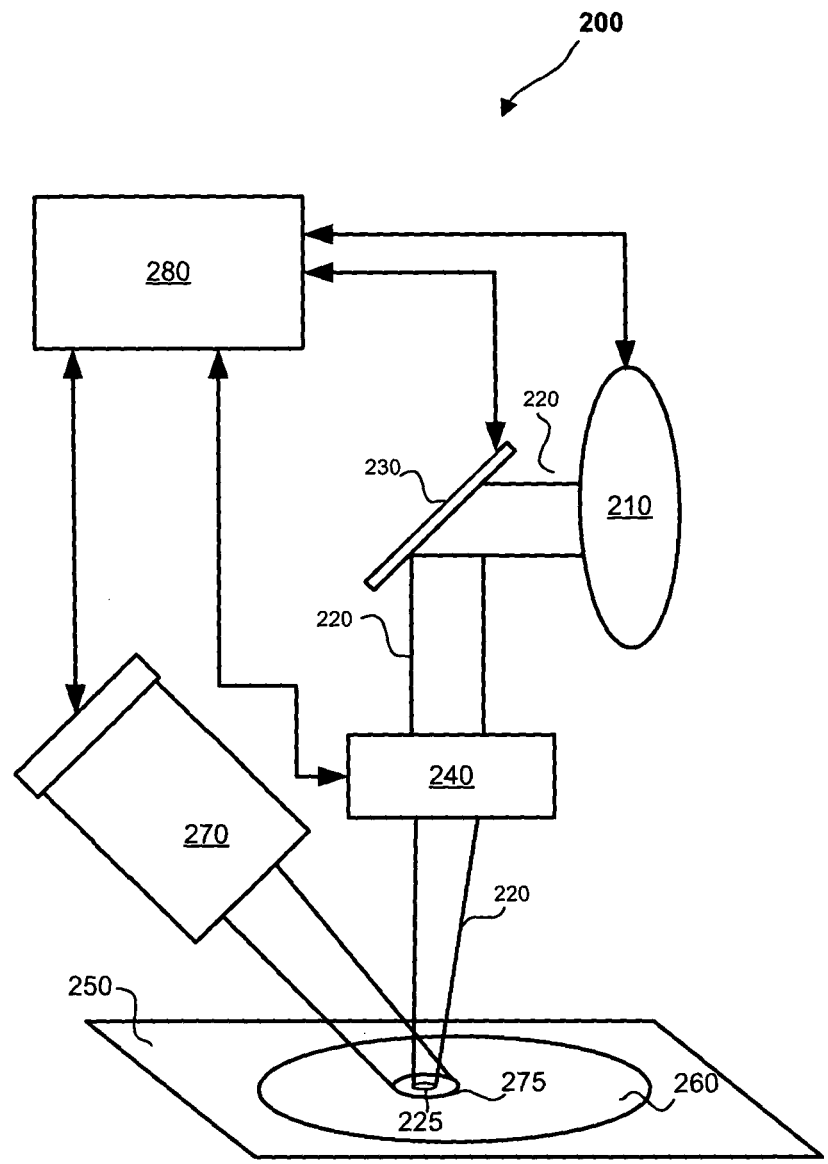
FIG. 2 is a systematic illustration of a laser ablation system in accordance with the present invention.

FIG. 2 is a systematic illustration of a laser ablation system in accordance with the present invention. Similar to the conventional laser ablation system 100 in FIG. 1, the inventive laser ablation system 200 in FIG. 2 has laser device 210 for generating laser beam 220, which is reflected by mirror 230, processed by an optical device 240 and focused on ablation target 250. The focused laser beam 220 projects laser spot 225 onto ablation field 260. For a given ablation spot, the ablation process uses the focused laser beam 220 to remove a surface material on the small spot where the laser beam 220 is focused on to form laser spot 225.

As shown in FIG. 2, the present invention improves the conventional laser ablation systems and methods by providing a monitoring and feedback mechanism to optimize the ablation effect. Laser ablation system 200 uses a probing device 270 to monitor observing area 275, which desirably covers laser spot 225 but is not required to be identical or closely matching laser spot 225. The probing device 270 measures an indicative property of observing area 275 or an indicative property of laser spot 225 projected on ablation field 260. The probing device 270 then generates a feedback signal according to the measured indicative property, and sends the feedback signal to control unit 280. Control unit 280 is in communication with laser device 210, mirror 230, optical device 240, and the probing device 270. Upon receiving the feedback signal from the probing device 270, control unit 280 adjusts an output parameter of pulsed laser 220 according to the feedback signal to optimize ablation effect. As discussed in further detail in a later section of the present disclosure, the adjusted output parameter of pulsed laser 220 may be any one or a combination of pulse energy, pulse rate, pulse duration, optical focusing, working distance, and scan speed. The adjustment of the output parameter of pulsed laser 220 may be achieved at any laser stage (including at laser device 210, mirror 230, or optical device 240), or a combination of several stages, depending on the design and desired purpose. Herein, the term "pulse rate" refers to the "pulse repetition rate" of a pulse train and the two terms are used interchangeably in this description.

Figure 3:
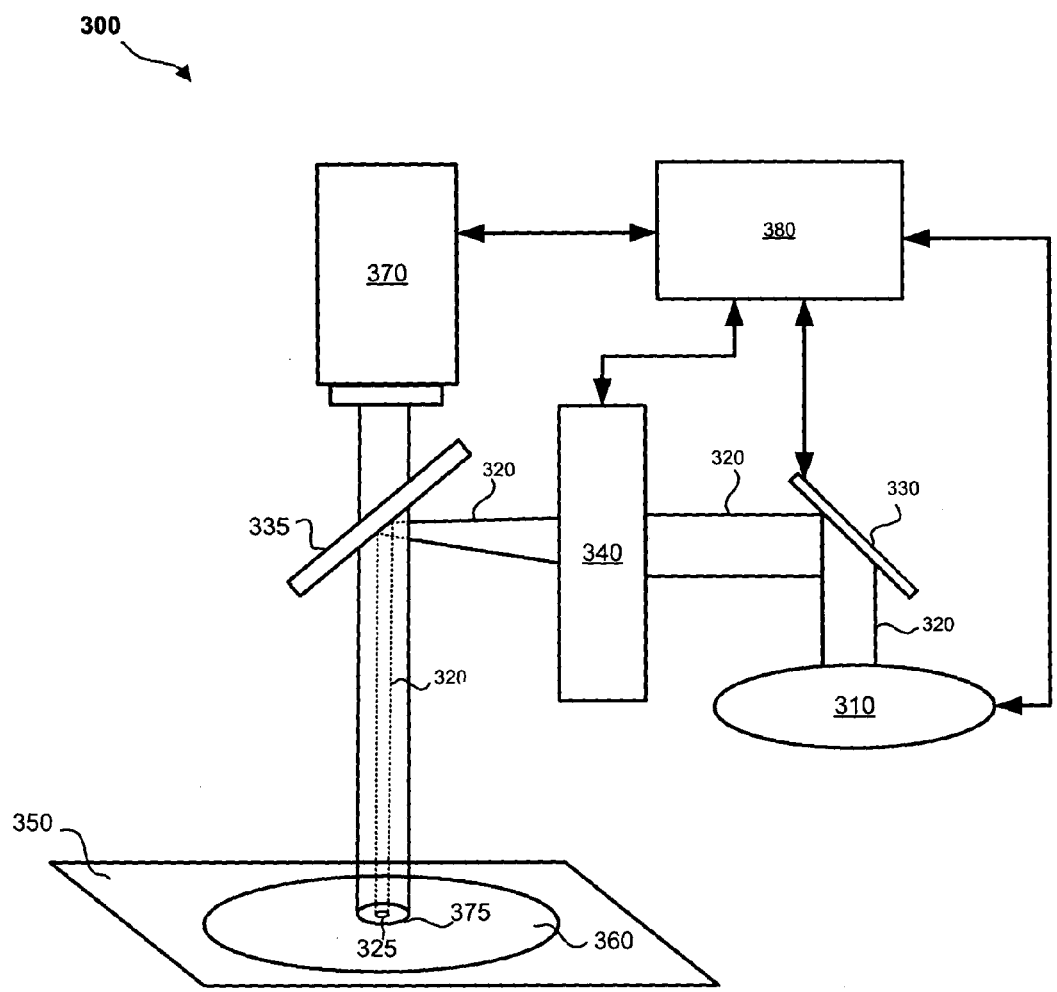
FIG. 3 is a systematic illustration of an alternative embodiment of the laser ablation system in accordance with the present invention.

FIG. 3 is a systematic illustration of an alternative embodiment of the laser ablation system in accordance with the present invention. Similar to laser ablation system 200 in FIG. 2, laser ablation system 300 in FIG. 3 has laser device 310 for generating laser beam 320, which is reflected by mirror 330, processed by an optical device 340 and focused on ablation target 350. The focused laser beam 320 projects laser spot 325 in ablation field 360. At any given ablation spot, laser ablation process uses the focused laser beam 320 to remove a surface material on the small spot where the laser beam 320 is focused on to form laser spot 325. Laser ablation system 300 uses a probing device 370 to monitor observing area 375, which desirably covers laser spot 325 but is not required to be identical or closely matching laser spot 325. The probing device 370 measures an indicative property of observing area 375 or an indicative property of laser spot 325 projected on ablation field 360. The probing device 370 then generates a feedback signal according to the measured indicative property, and sends the feedback signal back to control unit 380. Control unit 380 is in communication with laser device 210, mirror 230, optical device 240, and the probing device 370. Upon receiving the feedback signal from the probing device 370, control unit 380 adjusts an output parameter of pulsed laser 320 according to the feedback signal to optimize ablation effect.

Laser ablation system 300 differs from laser ablation system 200 in the following aspects: in laser ablation system 300, the probing device 370 shares a section of light path with pulsed laser 320, as facilitated by split mirror 335 which reflects pulsed laser 320 but is at least partially transparent to the light used by the probing device 370. In contrast, in laser ablation system 200, the light path of the probing device 270 is separate from that have pulsed laser 220. The design of laser ablation system 300 may help reducing the overall size of the apparatus.

The laser ablation systems 200 and 300 illustrated above are further explained below.

1. Examples of the Indicative Property Monitored

The indicative property monitored and measured in accordance with the present invention may be characteristic of either the ablation target or the pulsed laser that has been projected on the ablation target, or a combination thereof. The choice of indicative property to be measured is based on consideration of multiple parameters to ensure proper laser ablation. Such consideration includes:

(1) For laser ablation to occur, the laser beam projected on the target needs to have an optimal pulse energy density, which is defined as an energy density (or light intensity) of an individual pulse at a level or within a range of levels suitable for performing a desired ablation on the target material. For laser ablation of a given material, a minimum level of light intensity, called threshold light intensity, is required for ablation to occur. In the context of laser ablation, therefore, an optimal pulse energy density is generally near or above the threshold pulse energy density for laser ablation of the target material. For most materials, the optimal pulse energy density should also not be too much higher than (e.g., less than three times) the threshold pulse energy density. Often, surfaces of ablated materials are most efficiently ablated at pulse energy density about 2-4 times, or more preferably about 3 times, the ablation threshold.

(2) With a laser beam that has an operating pulse energy density, although ablation may occur, there still is a question of whether a desired amount of ablation is taking place and whether the ablation is occurring at an appropriate rate. This in turn relates to many factors such as pulse energy, pulse rate, and scanning speed.

Based on the above consideration, several embodiments utilizing different indicative properties are described below.

In one embodiment, the indicative property is indicative of the size of laser spot 225/325 projected on ablation field 260/360. For instance, the indicative property may be a diameter of laser spot 225/325 projected on ablation field 260/360. The diameter of laser spot 225/325 is then used to calculate or estimate the size of laser spot 225/325. Knowledge of the size of the laser spot 225/325 projected on the ablation field 260/360 is very beneficial. Although the cross-section of laser beam 220/320 is an inherent property of the beam itself, and could be measured within the laser device itself without requiring first projecting the laser beam 220/320 onto the ablation field 260/360 to form an actual ablation spot 225/325, it is preferred to measure the actual size of the projected laser beam spot 225/325. This is because the actual size of the projected laser spot 225/325 depends on many other factors in addition to the inherent cross-section size of the laser beam 220/320. These extra factors include the exact working distances such as front working distance between the working surface (ablation field 260/360) and the focusing optics 240/340, the characteristics of the working surface (ablation field 260/360), and the laser beam quality. For example, with a laser having a cross-section of about 10 μm in diameter, a front working distance of about 100 μm, the actual size of the projected laser spot on the working surface may still vary within a range of 2× from a minimum spot size to a maximum spot size. For highly effective and precise laser ablation, even a 5% of variation may be significant. Precisely monitoring the actual size of the projected laser spot is therefore highly beneficial for more accurate control and more efficient use of the laser system.

The measured actual size of the projected laser spot is a direct indicator of the effective pulse energy density applied at the corresponding ablation spot. For example, pulse energy density of the pulsed laser 220 may be obtained by calculating the ratio between pulse energy and the size of laser spot 225. This is possible because the pulse energy itself may be known or otherwise measured or calculated based on the parameters of the laser device generating the pulsed laser for ablation. Even if such quantitative information of pulse energy is unavailable or available but not accurate enough, the actual size of the projected laser spot can still be used as a guide of the relative level of pulse energy density. For example, if a particular spot size is known to result in a sufficient or optimum pulse energy density for ablation, that spot size may be used as a reference and compared against the measured actual size of the projected laser spot.

Figure 4:
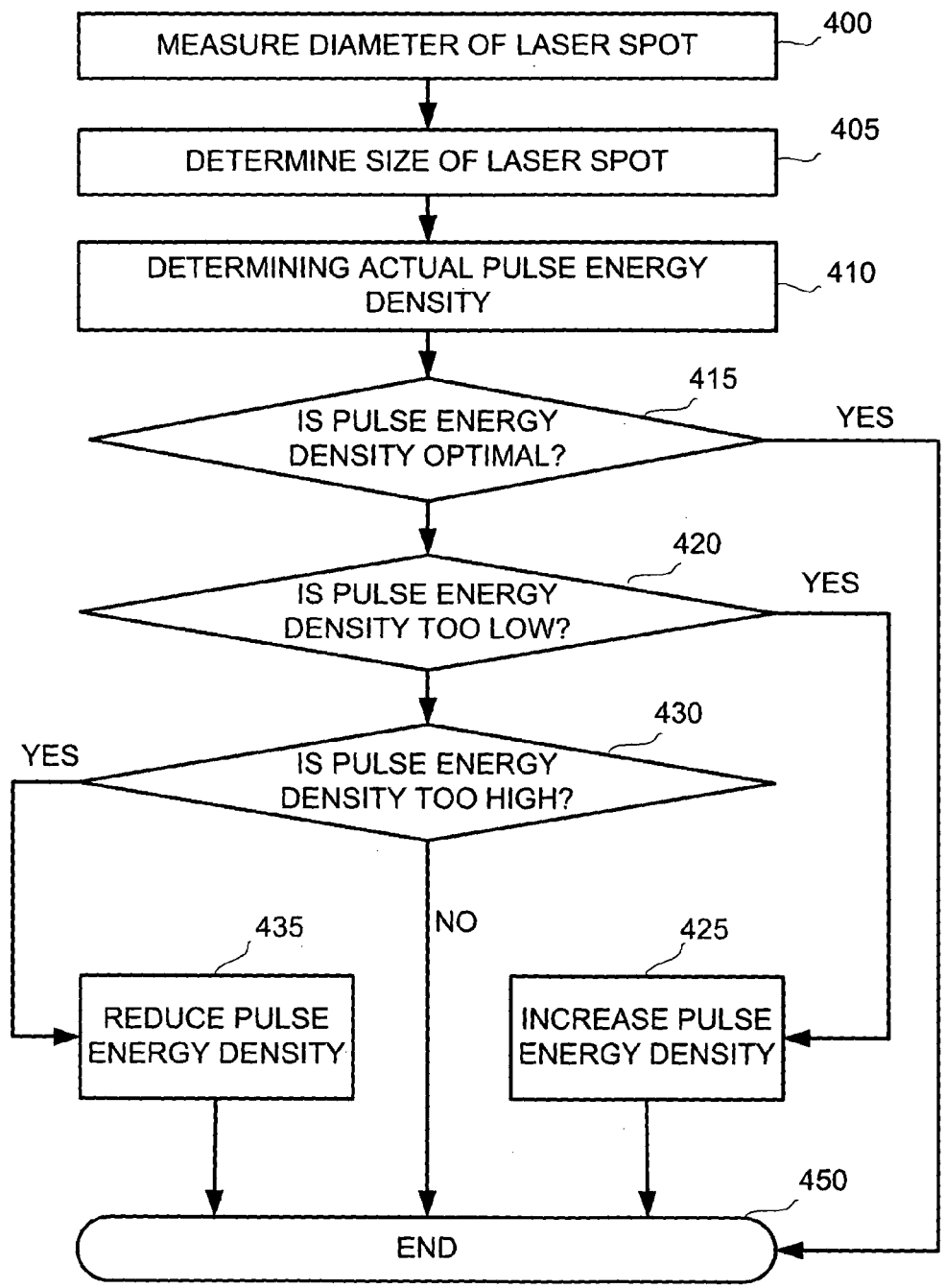
FIG. 4 is a block diagram showing an exemplary procedure of the monitoring and feedback mechanism of the present invention.

Based on the above information, a feedback signal is then determined. For example, if the measured pulse energy density is lower than a known minimum optimal pulse energy density for the effective laser ablation of a given material, a feedback signal for increasing the pulse energy density is generated. Conversely, if the measured pulse energy density is higher than a known maximum optimal pulse energy density, a feedback signal for decreasing the pulse energy density is generated. It is noted that for a given material, the ablation threshold is measured by pulse density, instead of pulse energy itself (the relation between the two is analogous to that between pressure and force). The threshold pulse density varies with different materials. If the pulse density is lower than the threshold, ablation would not occur. If the pulse energy is too high, ablation may not be optimally effective or may cause undesired problems such as thermal damages. An exemplary procedure of the above monitoring and feedback mechanism is shown in a block diagram of FIG. 4.

The pulse energy density can be modified, as discussed herein, by varying the optical amplifier pump power, or varying the size of the projected laser spot.

A variety of suitable devices or equipment, including a camera, a video camera, an infrared camera, a UV camera, a vidicon camera, a television camera remote to the ablation target (250 or 350), or an in vivo camera, may be used as the probing device (270 in FIG. 2 or 370 in FIG. 3) to measure the size of a projected laser spot. A variety of circuits can be used to determine a spot size from a video signal. One technique that may be used for determining the diameter of a generally circular spot, is to measure the sweep times of the reflections from the ablation pulse (e.g., 220 or 320) and use the longest sweep time as an indication of the spot diameter. However, those skilled in the art will recognize that other methods of determining the diameter of a generally circular spot could also be used.

In one exemplary embodiment, an image of the projected laser spot 225/325 may be projected onto a CCD array for monitoring purpose. In addition to obtaining the size information of the projected laser spot 225/325, the image formed on the CCD may also be used to determine the pulse beam quality during the ablation process.

In addition to directly measuring the diameter or the size of the projected laser spot, indirect methods may also be used to characterize the diameter or the size of the projected laser spot. An exemplary method is to first characterize the relationship between the size of the projected laser spot and the front working distance from the focusing optics (e.g., 240 or 340) to the ablation target 250/350, then determine the actual working distance during laser operation and use the distance information to further determine the actual size of the projected laser spot. The characterization of the above size-distance relationship may be done by the manufacturer and provided as a factory setting, or performed by a user of the ablation system of the present invention. The distance measurement can be performed with many techniques, such as optical reflectometry, OCT (optical coherence tomography), pulse time of flight measurements, ultrasound, etc.

In some embodiments, the indicative property being measured is indicative of progress of an ablation process on the ablation field 260/360. Accordingly, the output parameter of the pulsed laser 220/320 may be adjusted by increasing pulse energy if the indicative property indicates that no substantial ablation is taking place, and by changing pulse rate if the indicative property indicates an ablation rate deviating from a desired material removal rate.

For example, probing device 270/370 may be used to monitor a spot area on the surface of the ablation target that is being ablated. This monitoring may be performed either in place of or in addition to monitoring the projected laser spot 225/325. For instance, visual information may be collected from the monitored spot on the surface of the ablation target 250/350 to determine whether ablation is occurring, and if occurring whether a desired amount of ablation is taking place, and whether the ablation is occurring at an appropriate rate. The ablation system then generates a feedback signal based on the above determination, and adjusts an output parameter of the pulsed laser according to the feedback signal to optimize ablation effect. As discussed in further detail in a later section of the present disclosure, the output parameter that can be adjusted for this purpose may include pulse energy, pulse rate, pulse duration, working distance, optical focusing, and scanning speed.

In some embodiments, the indicative property being measured is a material composition of the ablation target. This may be done either in addition to or in place of measuring the size of the projected laser spot. One way of determining the composition of the material being ablated is sampling an ablation plume using a suitable spectroscopic method, such as Laser Induced Breakdown Spectroscopy (LIBS) and other types of emission spectroscopy.

In one embodiment, for example, the probing device 270/370 is a Laser Induced Breakdown Spectroscopy (LIBS) used for measuring the chemical composition of the party to material being ablated. LIBS is a type of atomic emission spectroscopy which utilizes a highly energetic laser pulse as the excitation source. LIBS can analyze a broad range of matter regardless of its physical state, be it solid, liquid or gas. Because all elements emit light when excited to sufficiently high temperatures, LIBS can detect all elements, limited only by the power of the laser as well as the sensitivity and wavelength range of the spectrograph & detector.

LIBS operates by focusing a laser onto a small area at the surface of the specimen, when the laser is discharged it ablates a very small amount of material, in the range of 1 μg, which instantaneously superheats generating a plasma plume with temperatures of ~10,000° C. At these temperatures the ablated material dissociates (breaks down) into excited ionic and atomic species. During this time the plasma emits a continuum of radiation which does not contain any useful information about the species present. But within a very small timeframe the plasma expands at supersonic velocities and cools, at this point the characteristic atomic emission lines of the elements can be observed.

A typical LIBS system has its own laser system, such as a Neodymium doped Yttrium Aluminium Garnet (Nd:YAG) solid state laser. When used in combination of the laser ablation system in accordance with the present invention, however, the sampling may be taken directly from the plume generated by the main laser (e.g., laser 220 in FIG. 2 or laser 320 in FIG. 3) for ablation, as an alternative to carrying out a separate ablation using a second laser just for sampling.

The information for the chemical composition of the target material being ablated may be used beneficially in the feedback mechanism in accordance to the present invention. Because the threshold pulse energy density required for laser ablation is material-dependent, the information for the chemical composition of the target material being ablated may be used to assist optimizing pulse energy density. For example, given the knowledge of material composition of the target material at the spot that is being ablated, a threshold pulse energy density or an optimal pulse energy density may be determined according to the spot-specific composition knowledge. Determining the threshold pulse energy density or the optimal pulse energy density may be done using empirical data, theoretical predictions, or a combination of both. The pulse energy density of the projected pulsed laser on the ablation target is then adjusted to match the threshold pulse energy density or the optimal pulse energy density determined according to the material composition of the ablation target.

Alternatively, the ablation system may be pre-calibrated for multiple settings each corresponding to a particular material composition. As the actual composition of the target material is determined, the ablation system may either automatically select or allow the user to select a setting among the multiple settings to match the composition.

Furthermore, it is appreciated that the knowledge of the material composition obtained with LIBS and the size of the projected laser spot can be combined to optimize the pulse energy for effective non-thermal ablation.

The step of measuring the indicative property and the step of adjusting an output parameter of the pulsed laser may be performed automatically and further dynamically. For example, the probing device 270/370 may measure the indicative property simultaneously as the ablation system 200/300 performs ablation, and send the feedback signal to control unit 280/380 immediately. Upon receiving the feedback signal, control unit 280/380 may perform the adjustment of one or more proper output parameters without having to first pause or stop the ablation.

2. Examples of the Adjustable Output Parameter of the Pulsed Laser

Several output parameters of the pulsed laser may be adjusted, either individually or in combination, to adjust and optimize the ablation effect in accordance with the present invention. These adjustable output parameters include but not limited to individual pulse energy, pulse rate, pulse duration, optical focus, working distance, and scanning speed.

An exemplary output parameter of the pulsed laser that may be adjusted to optimize the ablation effect is pulse energy, defined in the present description as the energy of an individual laser pulse. Because pulse energy density is pulse energy per unit area, changing pulse energy proportionally changes pulse energy density at a given size of projected laser spot on the ablation target. For example, the pulse energy can be increased if the pulse energy density of the pulsed laser is lower than a predetermined threshold or optimal level, and decreased if the pulse energy density of the pulsed laser is higher than the predetermined threshold or optimal level.

In one embodiment, changing pulse energy is accomplished by changing a pump current of a pump diode pumping the laser device. This can be implemented in a variety of laser devices suitable for generating laser for the purpose of the present invention. All lasers contain an amplifying medium, an energized substance that can increase the intensity of light that passes through it. The amplifying medium can be a solid, a liquid or a gas. In Nd:YAG laser, for example, the amplifying medium is a rod of yttrium aluminium garnate (YAG) containing neodymium ions. In a dye laser, it is a solution of a fluorescent dye in a solvent such as methanol. In a helium-neon laser, it is a mixture of the gases helium and neon. In a laser diode, it is a thin layer of semiconductor material sandwiched between other semiconductor layers. In many common laser devices, there is a "pumping" stage to energize the amplifying medium. Pumping changes the pulse energy, generally by changing the gain, the factor by which the intensity of the light is increased by the amplifying medium. Pumping may be performed either electrically or optically, but in either case a current may be changed to adjust, either directly or indirectly, the pulse energy, as further discussed below.

One embodiment of the present invention uses a type of laser devices in which one or more semiconductor optical amplifiers (SOA) are used for amplifying the laser. One or more SOAs are electrically pumped (rather than optically pumped by a separate laser diode). In this embodiment, a control unit (e.g., 280 or 380) changes the electrical pumping current to effectively control the pulse energy that comes out of the SOA.

Another embodiment of the present invention uses a type of laser devices in which a fiber optical amplifier (in contrast with an SOA) is used to amplify the pulse, and the fiber optical amplifier is optically pumped by a separate pump laser diode. In this embodiment, a control unit (e.g., 280 or 380) changes the current of the pumping diode to adjust the pulse energy produced by the fiber optical amplifier.

Yet another embodiment of the present invention uses a type of laser devices in which one or more semiconductor optical amplifiers (SOA) are used as preamplifiers, and a fiber optical amplifier (in contrast with an SOA) is used in the main amplification stage to amplify the pulse. The fiber optical amplifier is optically pumped by a separate pump laser diode. In this embodiment, a control unit (e.g., 280 or 380) changes the current of the pumping diode to adjust the pulse energy produced by the fiber optical amplifier.

One advantage of adjusting pulse energy by changing the pump current is that it makes it possible to control pulse energy density and ablation rate independently and separately.

Alternatively, the output parameter of the pulsed laser being adjusted is the pulse rate of the pulsed laser. This can be done either in combination of or independent from adjusting pulse energy as described above. Generally, changing pulse rate does not affect pulse energy density. So in this sense, when the pulse energy density is out of an optimal range, changing pulse rate may not be able to correct the problem. However, when the pulse energy density is within an optimal range, changing pulse rate may effectively control ablation rate (the speed at which the target material is being ablated and removed).

In one embodiment, the pulse rate of the pulsed laser is adjusted by selecting a subset of pulses from a pulse train generated by the laser device, and directing only the selected subset of pulses to the ablation target. For example, selecting every other pulse from a complete pulse train will effectively reduce the pulse rate by half. Various selecting schemes, including constant pulse rate selection (in which the pulses are selected at a fixed interval such that the selected subset of pulses has a constant pulse rate) and variable pulse rate selection (in which the pulses are selected at a varying interval such that the selected subset of pulses has a variable pulse rate), may be used for the purpose of the present invention.

In another embodiment, the ablation system uses multiple parallel optical amplifiers and changes pulse rate by selecting a subset of multiple optical amplifiers for operation at a time. The use of one or more amplifiers in parallel train mode (with pulses from one amplifier being delayed to arrive one or more nanoseconds after those from another amplifier, for example) allows step-wise control of ablation rate independent of pulse energy density. For example, where a lower ablation rate is desired, one or more amplifiers can be shut down. This has a similar effect of scaling the pulse rate and also has an advantage of being able to alleviate the thermal burden on individual amplifiers by alternatively rotating among the optical amplifiers placed in operation. However, this may increase the cost and size of the equipment and may not be practical in certain applications.

The laser ablation systems and methods in accordance with the present invention may be incorporated in a scanning process of laser ablation, or any other suitable laser ablation process. When incorporated in a scanning process, the scanning speed is also available as an output parameter of the pulsed laser to be adjusted by the control unit (280 or 380) according to a feedback signal received from the probing device (270 or 370). As known in the art, laser ablation systems perform scanning over an ablation field (e.g., 260 or 360) by moving one or more mirrors (e.g., 230 or 330). Typically, two separate mirrors are used, one for X-axis scanning and the other four Y-axis scanning. If it is desirable that the pulsed laser for ablation always strikes the surface of the ablation target at a normal angle during scanning, sophisticated lens systems such as telecentric multi-lens systems may be used. In accordance with the present invention, the speed of scanning is adjusted according to the feedback signal from the probing device (e.g., 270 or 370) to ensure that a proper amount of material removal is taken place at each ablation spot.

With an optimal pulse energy density and a given pulse rate, the amount of material removed by laser ablation at a certain ablation spot depends on the effective time the projected laser spot (e.g., 225 or 325) spent at the ablation spot. The length of this effective time is determined by both the scanning speed and the cross-section diameter of the projected laser spot (e.g., 225 or 325). A higher scanning speed and a smaller diameter of the projected laser spot translate to a shorter effective ablation time at the ablation spot, and vice versa. If the feedback signal from the probing device (e.g., 270 or 370) indicates that an insufficient amount of material is being removed, the control unit (280 or 380) slows down the scanning to increase the effective ablation time and to thus increase the amount of material removal, and vice versa. This may be alternatively accomplished by adjusting the size of the projected laser spot, but caution must be taken because changing the size of the projected laser spot also changes the pulse energy density and would thus change the other aspects of the ablation is well.

3. Type of Lasers Used

For some applications, the pulsed laser desirably has short pulses. Some applications, for example, may prefer a pulse duration shorter than 1 picosecond, or a pulse duration shorter than 100 femtoseconds. For some applications, the pulse energy density of the pulsed laser ranges from about 0.1 Joules/cm$^2$ to about 20 Joules/cm$^2$.

A number of types of laser amplifiers have been used for generating short laser pulses for laser ablation. Techniques for generating these ultra-short pulses (USP) are described, e.g., in a book entitled "Femtosecond Laser Pulses" (C. Rulliere, editor), published 1998, Springer-Verlag Berlin Heidelberg New York. Generally large systems, such as Ti:Sapphire, are used for generating ultra-short pulses (USP).

The USP phenomenon was first observed in the 1970's, when it was discovered 25 that mode-locking a broad-spectrum laser could produce ultra-short pulses. The minimum pulse duration attainable is limited by the bandwidth of the gain medium, which is inversely proportional to this minimal or Fourier-transform-limited pulse duration.

Mode-locked pulses are typically very short and will spread (i.e., undergo temporal dispersion) as they traverse any medium. Subsequent pulse-compression techniques are often used to obtain USP's. Pulse dispersion can occur within the laser cavity so that compression techniques are sometimes added intra-cavity. When high-power pulses are desired, they are intentionally lengthened before amplification to avoid internal component optical damage. This is referred to as "Chirped Pulse Amplification" (CPA). The pulse is subsequently compressed through pulse-duration compression to obtain short pulses with a high peak power.

For example, the laser device may first generates wavelength-swept-with-time pulses from an oscillator-driven semiconductor pulse generator, have the initial pulses amplified by a fiber-amplifier, e.g., a erbium-doped fiber amplifier (or EDFA) or a Cr:YAG amplifier and then compressed by an air-path between gratings compressor such as a Treacy grating compressor is an air-grating compressor. The compression creates sub-picosecond ablation pulse. The pulses having a pulse duration between one nanosecond and 10 picoseconds may be generated using this technique.

The use of optical-amplifier/compressor allows a reduction in ablation system size, enabling the system to be man-portable. For example the system including an oscillator, amplifier and compressor may be transported as a wheeled cart or a backpack.

The present invention improves the controllability and precision by using a feedback loop monitoring the ablation target that is being ablated. This invention can be used for various types of laser ablation, particularly for use as a medical surgical tool. Ablative material removal with short laser pulses can be done either in-vivo and/or on the body surface. As illustrated herein, in some embodiments, a desired pulse energy density is first set for the material being ablated, the optical pumping power is then fine-tuned by dynamic feedback from a probing device which can be a spot-size sensor. Controlling the optical pumping power by dynamic feedback is useful with handheld ablation probes and in instances that diameter of the projected laser spot varies by more than +/−10%. In some embodiments, dynamic feedback control the present invention may have pulse energy control and/or pulse rate control as primary control and thus require very little or none optical control of the size of the projected laser spot through optical focusing mechanism. Such embodiments allow the requirements for the optical system such as focusing ability and optical focal length, to be relaxed, thus reducing the cost of the system.

The above description, including the specification and drawings, is illustrative and not restrictive. Many variations of the invention will become apparent to those of skill in the art upon review of this disclosure. Various features and aspects of the above-described disclosure may be used individually or jointly. Further, the present disclosure can be utilized in any number of environments and applications beyond those described herein without departing from the broader spirit and scope of the specification. The scope of the invention should, therefore, be determined not with reference to the above description, but instead should be determined with reference to the appended claims along with their full scope of equivalents. In addition, it will be recognized that the terms "comprising," "including," and "having," as used herein, are specifically intended to be read as open-ended terms of art. The term "or" as used herein is not a logic operator in an exclusive sense unless explicitly described as such.

What is claimed is:

1. A laser ablation method comprising:
   generating an ultrashort pulsed laser using a laser device;
   projecting the ultrashort pulsed laser onto an ablation target to be ablated;
   measuring an indicative property of the ablation spot-size;
   generating a feedback signal according to the measured indicative property;
   feeding the feedback signal to a control unit; and
   adjusting an output parameter of the ultrashort pulsed laser according to the feedback signal to optimize ablation effect.

2. The method of claim 1 wherein the indicative property is indicative of a size of a laser beam spot projected on the ablation target.

3. The method of claim 2 wherein the indicative property comprises a diameter of the laser beam spot.

4. The method of claim 2 wherein the feedback signal is determined according to a pulse energy density of the ultrashort pulsed laser defined as a ratio between pulse energy and the size of the laser beam spot.

5. The method of claim 4 wherein the step of adjusting an output parameter of the ultrashort pulsed laser comprises:
   increasing the pulse energy if the pulse energy density of the ultrashort pulsed laser is lower than a predetermined threshold or optimal level; or
   decreasing the pulse energy if the pulse energy density of the ultrashort pulsed laser is higher than the predetermined threshold or optimal level.

6. The method of claim 1 wherein the step of adjusting an output parameter of the ultrashort pulsed laser comprises changing pulse energy.

7. The method of claim 6 wherein changing pulse energy comprises changing a pump current of a pump diode pumping the laser device.

8. The method of claim 1 wherein the step of adjusting an output parameter of the ultrashort pulsed laser comprises changing pulse rate of the pulsed laser.

9. The method of claim 8 wherein changing pulse rate of the ultrashort pulsed laser comprises selecting a subset of pulses from a pulse train generated by the laser device and projecting the selected subset of pulses unto the ablation target.

10. The method of claim 1 wherein the indicative property is measured using an optical probe.

11. The method of claim 10 wherein the optical probe comprises a camera.

12. The method of claim 1 wherein the indicative property comprises a material composition of the ablation target.

13. The method of claim 12 wherein the material composition is measured by sampling an ablation plume.

14. The method of claim 12 wherein the material composition is measured by a Laser Induced Breakdown Spectroscopy (LIBS).

15. The method of claim 12 further comprising:
   determining a threshold pulse energy density or an optimal pulse energy density according to the material composition of the ablation target;
   determining an actual pulse energy density of the ultrashort pulsed laser projected on the ablation target; and
   comparing the actual pulse energy density with the threshold pulse energy density or the optimal pulse energy density.

16. The method of claim 15 wherein the step of adjusting an output parameter of the ultrashort pulsed laser comprises adjusting pulse energy to match a resultant pulse energy density of the ultrashort pulsed laser projected on the ablation target with the threshold pulse energy density or the optimal pulse energy density determined according to the material composition of the ablation target.

17. The method of claim 12 further comprising measuring a size of the laser beam spot projected on the ablation target.

18. The method of claim 1 wherein the indicative property is indicative of progress of an ablation process on the ablation target.

19. The method of claim 18 wherein the step of adjusting an output parameter of the ultrashort pulsed laser comprises:
   increasing pulse energy if the indicative property indicates that no substantial ablation is taking place; and
   changing pulse rate if the indicative property indicates an ablation rate deviating from a desired material removal rate.

20. The method of claim 1 wherein the step of measuring the indicative property and the step of adjusting an output parameter of the ultrashort pulsed laser are performed dynamically.

21. The method of claim 1 further comprising measuring an indicative property of the ultrashort pulsed laser projected on the ablation target.

* * * * *